United States Patent
Kori et al.

(10) Patent No.: US 12,379,661 B2
(45) Date of Patent: Aug. 5, 2025

(54) MATERIAL FOR FORMING ORGANIC FILM, SUBSTRATE FOR MANUFACTURING SEMICONDUCTOR DEVICE, METHOD FOR FORMING ORGANIC FILM, PATTERNING PROCESS, AND COMPOUND FOR FORMING ORGANIC FILM

(71) Applicant: SHIN-ETSU CHEMICAL CO., LTD., Tokyo (JP)

(72) Inventors: Daisuke Kori, Joetsu (JP); Takashi Sawamura, Joetsu (JP); Hironori Satoh, Joetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 937 days.

(21) Appl. No.: 17/487,150

(22) Filed: Sep. 28, 2021

(65) Prior Publication Data
US 2022/0107566 A1  Apr. 7, 2022

(30) Foreign Application Priority Data
Oct. 5, 2020 (JP) .................... 2020-168278

(51) Int. Cl.
 G03F 7/11 (2006.01)
 C07D 519/00 (2006.01)
 (Continued)

(52) U.S. Cl.
CPC .............. *G03F 7/11* (2013.01); *C07D 519/00* (2013.01); *H01L 21/0338* (2013.01); (Continued)

(58) Field of Classification Search
CPC ... G03F 7/11; G03F 7/004; G03F 7/09; G03F 7/094; G03F 7/2004; G03F 7/32; C07D 519/00; C07D 491/22
See application file for complete search history.

(56) References Cited

U.S. PATENT DOCUMENTS

| 4,276,407 A | 6/1981 | Bilow et al. |
|---|---|---|
| 2002/0106909 A1 | 8/2002 | Kato et al. |

(Continued)

FOREIGN PATENT DOCUMENTS

| CN | 104130177 A | 11/2014 |
|---|---|---|
| CN | 110499137 A | 11/2019 |

(Continued)

OTHER PUBLICATIONS

Jul. 21, 2021 Extended European Search Report in European Patent Application No. 21158303.4.

(Continued)

*Primary Examiner* — Walter H Swanson
(74) *Attorney, Agent, or Firm* — Oliff PLC

(57) ABSTRACT

The present invention is a material for forming an organic film, containing: (A) a compound for forming an organic film shown by the following general formula (1A); and (B) an organic solvent, where $W_1$ represents a tetravalent organic group, n1 represents an integer of 0 or 1, n2 represents an integer of 1 to 3, and $R_1$ represents any one or more of the following general formulae (1B). This provides an imide compound, where the compound is cured not only under air, but also under film formation conditions of inert gas, and can form an organic underlayer film having not only excellent heat resistance and properties of filling and planarizing a pattern formed on a substrate, but also favorable film formation and adhesion to a substrate, and a material for forming an organic film containing the compound.

(1A)

(Continued)

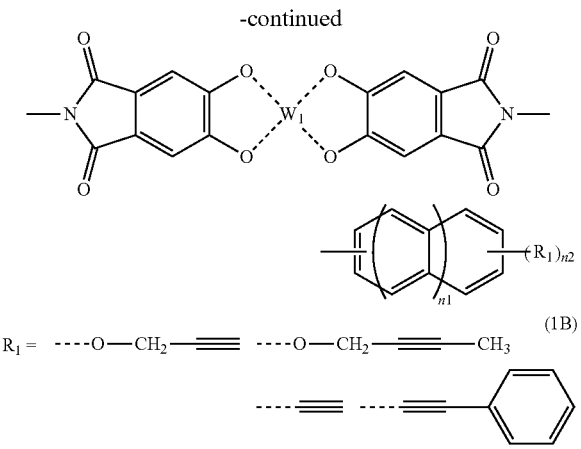

23 Claims, 4 Drawing Sheets

(51) Int. Cl.
H01L 21/033 (2006.01)
H01L 21/308 (2006.01)
H01L 21/311 (2006.01)
H01L 21/3213 (2006.01)

(52) U.S. Cl.
CPC .... H01L 21/3088 (2013.01); H01L 21/31144 (2013.01); H01L 21/32139 (2013.01)

(56) References Cited

U.S. PATENT DOCUMENTS

| | | |
|---|---|---|
| 2005/0255712 A1 | 11/2005 | Kato et al. |
| 2006/0019195 A1 | 1/2006 | Hatakeyama et al. |
| 2006/0204891 A1 | 9/2006 | Hatakeyama |
| 2009/0274978 A1 | 11/2009 | Ohashi et al. |
| 2010/0099044 A1 | 4/2010 | Hatakeyama et al. |
| 2012/0252217 A1 | 10/2012 | Minegishi et al. |
| 2013/0302990 A1 | 11/2013 | Watanabe et al. |
| 2016/0085152 A1 | 3/2016 | Nakafuji et al. |
| 2016/0222165 A1 | 8/2016 | Wakita et al. |
| 2016/0314984 A1 | 10/2016 | Matsumura et al. |
| 2017/0184968 A1 | 6/2017 | Kori et al. |
| 2020/0041903 A1 | 2/2020 | Takemura et al. |
| 2020/0166844 A1 | 5/2020 | Okada et al. |
| 2020/0231720 A1* | 7/2020 | Masuyama ........... G03F 7/0045 |
| 2020/0348595 A1 | 11/2020 | Nakafuji et al. |
| 2022/0107566 A1 | 4/2022 | Kori et al. |

FOREIGN PATENT DOCUMENTS

| | | |
|---|---|---|
| JP | 2002-334869 A | 11/2002 |
| JP | 2005-128509 A | 5/2005 |
| JP | 2006-285095 A | 10/2006 |
| JP | 2006-293298 A | 10/2006 |
| JP | 2007-137960 A | 6/2007 |
| JP | 2007-199653 A | 8/2007 |
| JP | 2009-269953 A | 11/2009 |
| JP | 2010-122656 A | 6/2010 |
| JP | 2010-181605 A | 8/2010 |
| JP | 2012-215842 A | 11/2012 |
| JP | 2013-137334 A | 7/2013 |
| JP | 2013-253227 A | 12/2013 |
| JP | 2016-044272 A | 4/2016 |
| JP | 2016-060886 A | 4/2016 |
| JP | 2017-119671 A | 7/2017 |
| KR | 10-2017-0076585 A | 7/2017 |
| KR | 10-2020-0014709 A | 2/2020 |
| WO | 2004/066377 A1 | 8/2004 |
| WO | 2014/208324 A1 | 12/2014 |
| WO | 2018/212116 A1 | 11/2018 |
| WO | 2019/146378 A1 | 8/2019 |

OTHER PUBLICATIONS

Grenier-Loustalot, M. et al., "Propargylic-terminated prepolymers. 5. Mechanistic and kinetic studies of the polymerization reaction of compounds with an imide group meta to the propargylic function," High Perform. Polym . . . , vol. 8, pp. 555-578, 1996.
Jun. 27, 2022 Office Action issued in Korean Patent Application No. 10-2021-0033609.
Mar. 24, 2023 Office Action Issued In U.S. Appl. No. 17/181,776.
U.S. Appl. No. 17/181,776, filed Feb. 22, 2022 in the name of Kori et al.
Kumar, U. et al., "Hybrid Polyimide-Polyphenylenes by the Diels-Alder Polymerization Between Biscyclopentadienones and Ethynyl-Terminated Imides," Water-Soluble Polymers: Synthesis, Solution Properties and Applications, American Chemical Society, vol. 614, pp. 518-526, 1995.
Nov. 21, 2023 Office Action issued in Japanese Patent Application No. 2021-015285.
Kumar, U. et al., "Hybrid Polyimide-Polyphenylenes by the Diels-Alder Polymerization Between Biscyclopentadienones and Ethynyl-Terminated Imides," Water-Soluble Polymers: Synthesis, Solution Properties and Applications, American Chemical Society, vol. 614, pp. 518-526, XP002047532.
Mar. 23, 2022 extended Search Report issued in European Patent Application No. 21200228.1.

* cited by examiner

[FIG. 1]
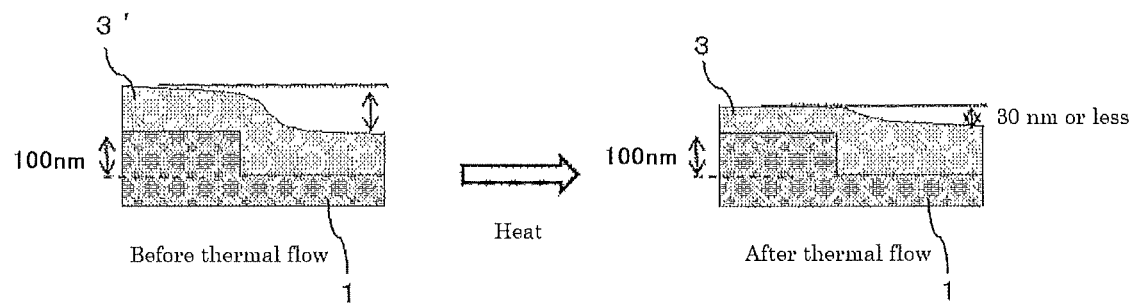
[FIG. 2]
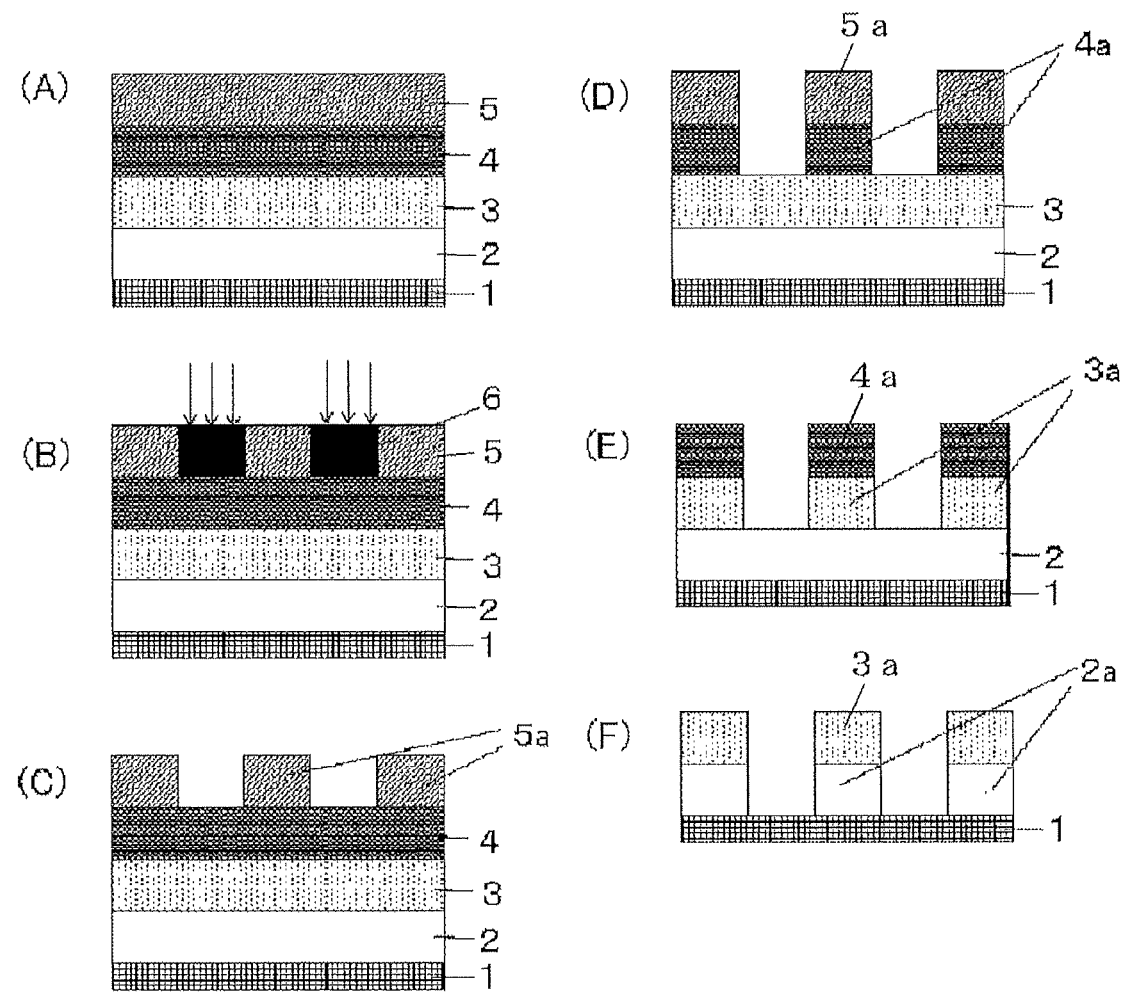

[FIG. 3]
(G)
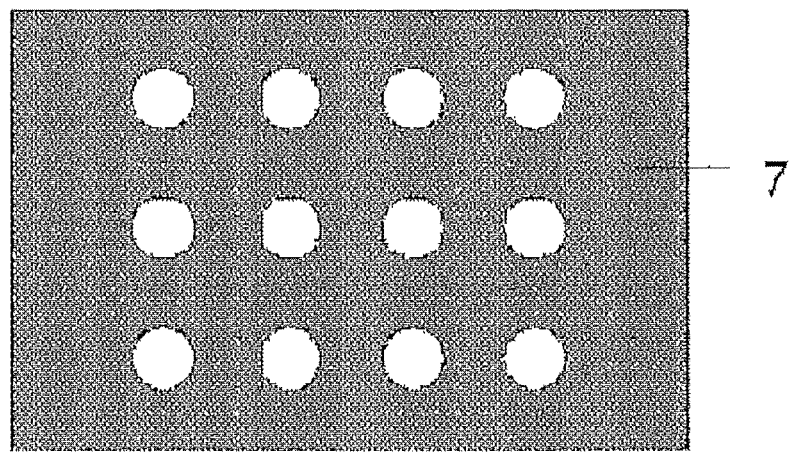
(H)
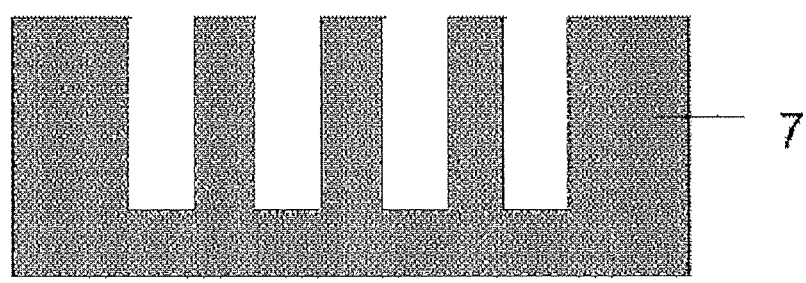
(I)
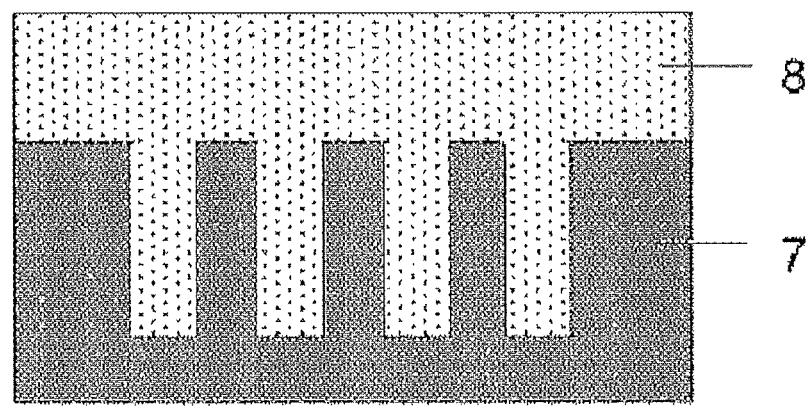

[FIG. 4]
(J)
(K)
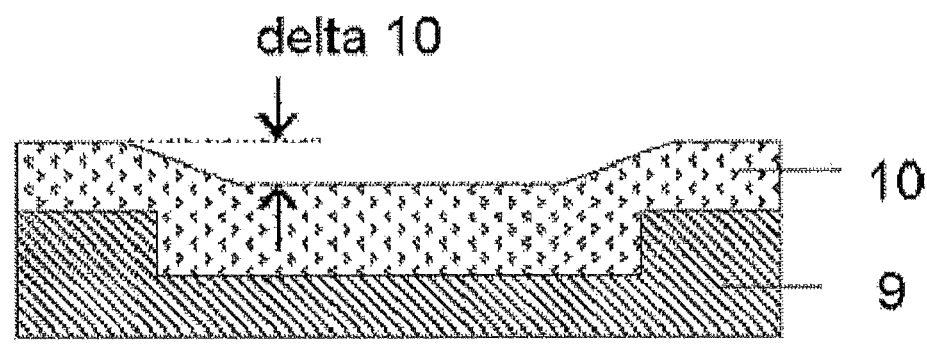

[FIG. 5]
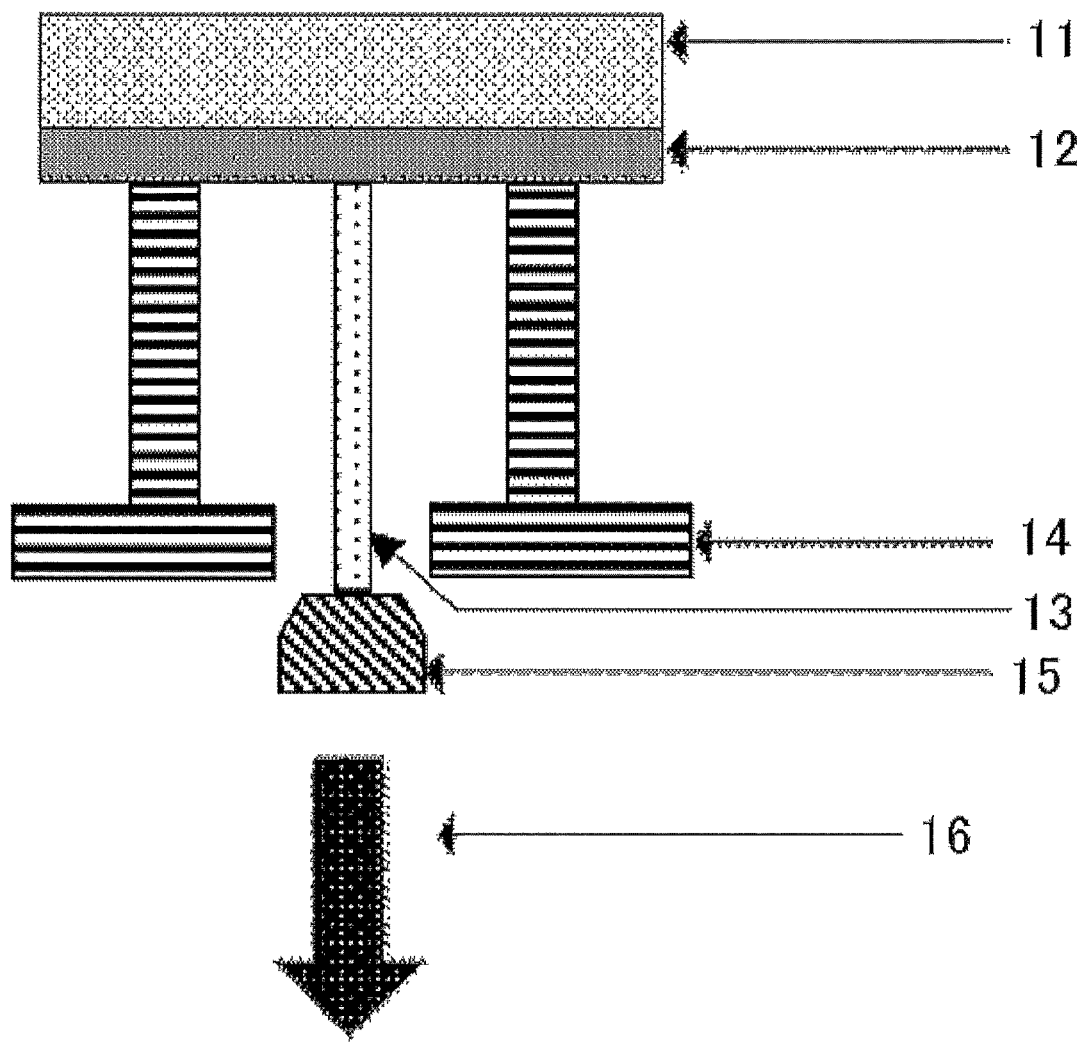

MATERIAL FOR FORMING ORGANIC FILM, SUBSTRATE FOR MANUFACTURING SEMICONDUCTOR DEVICE, METHOD FOR FORMING ORGANIC FILM, PATTERNING PROCESS, AND COMPOUND FOR FORMING ORGANIC FILM

TECHNICAL FIELD

The present invention relates to: a material for forming an organic film used in a semiconductor device manufacturing process; a substrate for manufacturing a semiconductor device using the material; a method for forming an organic film using the material; a patterning process according to a multilayer resist method using the material; and a compound for forming an organic film suitably used in the material.

BACKGROUND ART

Conventionally, high integration and high processing speed of semiconductor devices have been achieved through the miniaturization of pattern size by shortening the wavelength of light sources in lithography technology using light exposure (photolithography), which is commonly employed technology. To form such a fine circuit pattern on a substrate for a semiconductor device (substrate to be processed), the following method is generally employed in which the substrate to be processed is processed by dry-etching while using a patterned photoresist film as an etching mask. In practice, however, there is no dry-etching method capable of providing an absolute etching selectivity between the photoresist film and the substrate to be processed. Hence, recently, it has been common to process a substrate by a multilayer resist method. This method is as follows: first, a middle layer film having an etching selectivity different from that of a photoresist film (hereinafter, resist upper layer film) is placed between the resist upper layer film and a substrate to be processed; a pattern is formed in the resist upper layer film; then, the pattern is transferred to the middle layer film by dry-etching while using the resist upper layer film pattern as a dry-etching mask; furthermore, the pattern is transferred to the substrate to be processed by dry-etching while using the middle layer film as a dry-etching mask.

One of the multilayer resist methods is a 3-layer resist method which can be performed with a typical resist composition used in a monolayer resist method. In this method, a substrate to be processed is coated with an organic underlayer film material composed of an organic resin-containing composition and then baked to form an organic underlayer film (hereinafter, organic film); the organic film is subsequently coated with a resist middle layer film material composed of a composition containing a silicon-containing resin, and baked to form a silicon-containing film (hereinafter, silicon-containing resist middle layer film); thereafter, a typical organic photoresist film (hereinafter, resist upper layer film) is formed on the silicon-containing resist middle layer film. The resist upper layer film is patterned and then subjected to dry-etching with fluorine-based gas plasma, so that the resist upper layer film pattern can be transferred to the silicon-containing resist middle layer film. This is because the organic resist upper layer film can exhibit a favorable etching selectivity ratio relative to the silicon-containing resist middle layer film. This method allows a pattern to be easily transferred to the silicon-containing resist middle layer film even if a resist upper layer film does not have film thickness sufficient for directly processing the substrate to be processed or if a resist upper layer film does not have sufficient dry-etching resistance for processing the substrate to be processed. This is because the silicon-containing resist middle layer film generally has a film thickness equal to or smaller than that of the resist upper layer film. Subsequently, while using the silicon-containing resist middle layer film having the transferred pattern as a dry-etching mask, the pattern is transferred to the organic film by dry-etching with oxygen- or hydrogen-based gas plasma. Thereby, the pattern can be transferred to the organic film having dry-etching resistance sufficient for substrate processing. This organic film pattern having the transferred pattern can be transferred to the substrate by dry-etching with a fluorine-based gas, chlorine-based gas, or the like.

Meanwhile, the miniaturization in the semiconductor device manufacturing process is approaching the limit inherent in the wavelength of light sources for photolithography. Accordingly, recently, the high integration of semiconductor devices that does not rely on miniaturization has been examined. As one means for the high integration, semiconductor devices having complicated structures such as multigate structures have been examined, and some of these have already been put into practical use. In forming such structures by multilayer resist methods, it is possible to employ an organic film material which is capable of filling a fine pattern including hole, trench, and fin formed on a substrate to be processed with a film without void, and capable of filling a step- or pattern-dense region and a pattern-free region with a film to planarize the regions. The use of such an organic film material to form an organic film having a flat surface on a stepped substrate can reduce fluctuations in film thicknesses of a silicon-containing resist middle layer film and a resist upper layer film formed thereon, and can suppress reductions in a focus margin in photolithography and a margin in a subsequent step of processing the substrate to be processed. This makes it possible to manufacture semiconductor devices with high yields. On the other hand, in the monolayer resist method, the upper resist film has to have a large film thickness to fill a stepped or patterned substrate to be processed. As a result, for example, pattern collapse occurs after exposure and development, and the pattern profile deteriorates due to reflection from the substrate at exposure. Consequently, the pattern formation margin at exposure is narrowed, making it difficult to manufacture semiconductor devices with high yields.

Furthermore, as techniques for the high processing speed of next-generation semiconductor devices, for example, the application of the following materials have also started to be examined: novel materials having high electron mobility using strained silicon, gallium arsenic, and so forth; and high-precision materials such as ultrathin polysilicon controlled in units of angstrom. However, in substrates to be processed to which such novel high-precision materials are applied, the materials may be corroded by oxygen in air under conditions during the flat film formation from an organic film material as described above, for example, film formation conditions of air and 300° C. or higher. Hence, such a performance as a high processing speed of a semiconductor device according to the material design cannot be exhibited, and industrially satisfactory yield may not be achieved. For this reason, an organic film material capable of forming a film in an inert gas has been desired so as to avoid a decrease in yield due to substrate corrosion by air under such high temperature conditions.

Conventionally, condensed resins using aromatic alcohols and carbonyl compounds such as ketones and aldehydes as condensing agents for a phenol-based compound or naphthol-based compound have been known as materials for forming an organic film for multilayer resist methods. Examples of such condensed resins include a fluorene bisphenol novolak resin described in Patent Document 1, a bisphenol compound and a novolak resin thereof described in Patent Document 2, a novolak resin of an adamantane phenol compound described in Patent Document 3, a bisnaphthol compound and a novolak resin thereof described in Patent Document 4, and the like. Causing by a curing action due to crosslinking using a methylol compound as a crosslinking agent, or a curing action by a crosslinking reaction by oxidation at the α-position of an aromatic ring due to the action of oxygen in air and the subsequent condensation, such a material can form a film having solvent resistance in relation to a coating film material used in the subsequent step.

Furthermore, a material in which triple bonds are employed as intermolecular linking groups in a curable resin is known. For example, Patent Documents 5 to 10 are known. In these materials, a cured film having solvent resistance is formed not only by the methylol-derived crosslinking, but also by crosslinking due to polymerization with triple bonds. However, these materials for forming an organic film do not have sufficient filling property or sufficient planarizing property of a pattern formed on a substrate.

Moreover, as compounds having an imide structure, polyimide disclosed in Patent Document 11, imide compounds disclosed in Patent Document 12, etc. are exemplified as compounds having excellent heat resistance. However, heat resistance, flatness, adhesiveness to a substrate, and so forth are not sufficient, and there has been room for improvement.

CITATION LIST

Patent Literature

Patent Document 1: JP 2005-128509 A
Patent Document 2: JP 2006-293298 A
Patent Document 3: JP 2006-285095 A
Patent Document 4: JP 2010-122656 A
Patent Document 5: JP 2010-181605 A
Patent Document 6: WO 2014-208324 A1
Patent Document 7: JP 2012-215842 A
Patent Document 8: JP 2016-044272 A
Patent Document 9: JP 2016-060886 A
Patent Document 10: JP 2017-119671 A
Patent Document 11: JP 2013-137334 A
Patent Document 12: WO 2019-146378 A1

SUMMARY OF INVENTION

Technical Problem

The present invention has been made in view of the above circumstances. An object of the present invention is to provide: an imide compound, where the compound is cured not only under air, but also under film formation conditions of inert gas, and can form an organic underlayer film having not only excellent heat resistance and properties of filling and planarizing a pattern formed on a substrate, but also favorable film formation and adhesion to a substrate, and a material for forming an organic film containing the compound. Furthermore, the present invention also provides a substrate for manufacturing a semiconductor device using the material, a method for forming an organic film using the material, and a patterning process using the material.

Solution to Problem

To solve the above problems, the present invention provides a material for forming an organic film, comprising:

(A) a compound for forming an organic film shown by the following general formula (1A); and (B) an organic solvent,

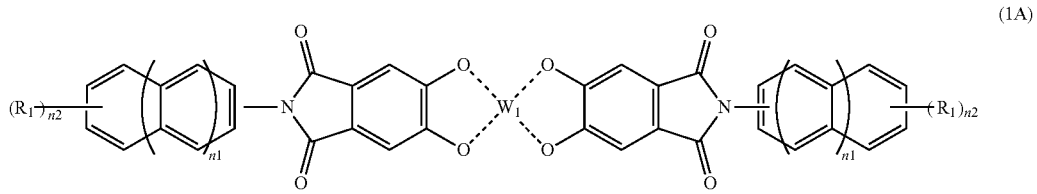

wherein $W_1$ represents a tetravalent organic group, n1 represents an integer of 0 or 1, n2 represents an integer of 1 to 3, and $R_1$ represents any one or more of the following general formulae (1B).

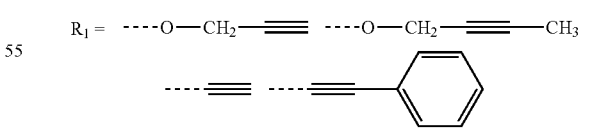

With such a material for forming an organic film, the composition for forming an organic film can form an organic film which is cured under film formation conditions of inert gas as well as air, and has high heat-resistance, favorable adhesion to a substrate, and high filling and planarizing properties.

Furthermore, the component (A) is preferably a compound shown by the following general formula (1C) or (1D),

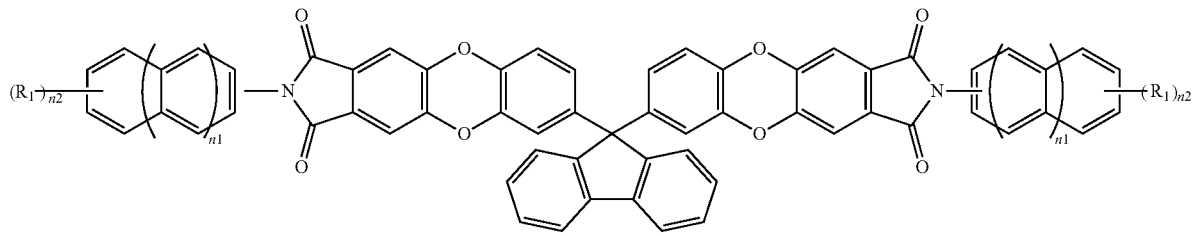

(1C)

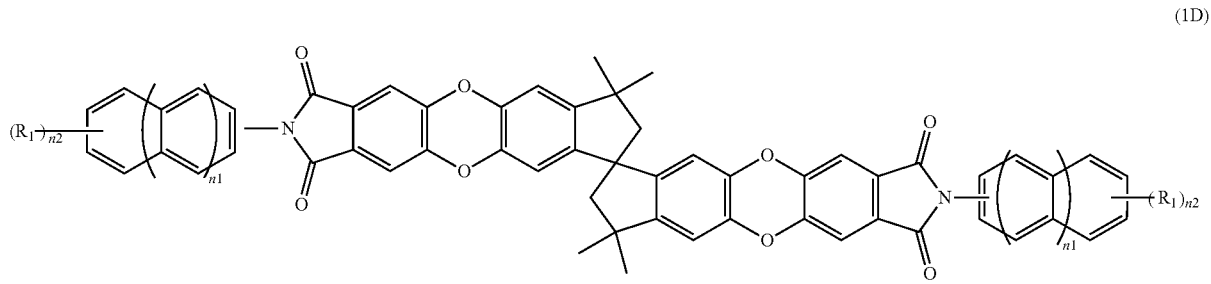

(1D)

wherein n1, n2, and $R_1$ in the formulae have the same meanings as defined above.

Intermolecular interaction between imide groups can be relieved and crystallinity can be inhibited by introducing a spiro structure or a cardo structure into the compound for forming an organic film as described above. In this manner, it becomes possible to improve solubility in an organic solvent and film formation, and to achieve both heat resistance and filling/planarizing properties, which are conflicting properties.

Furthermore, the component (A) is preferably a compound shown by the following general formula (1E) or (1F).

lar weight and Mn is a number average molecular weight measured by gel permeation chromatography in terms of polystyrene.

Controlling Mw/Mn of the compound for forming an organic film within such a range, an organic film excellent in filling property and planarizing property can be formed.

Furthermore, the component (B) is preferably a mixture of one or more kinds of organic solvent having a boiling point of lower than 180° C. and one or more kinds of organic solvent having a boiling point of 180° C. or higher.

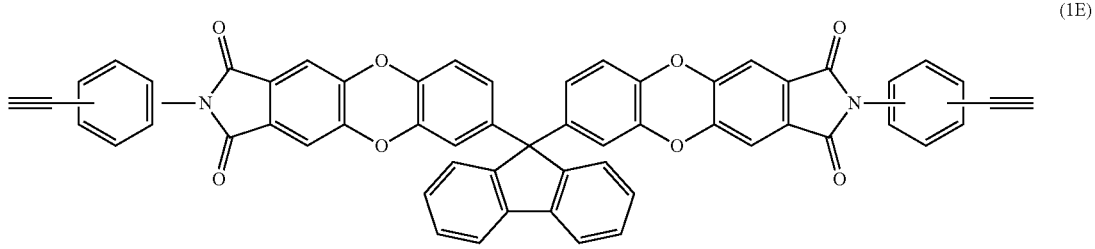

(1E)

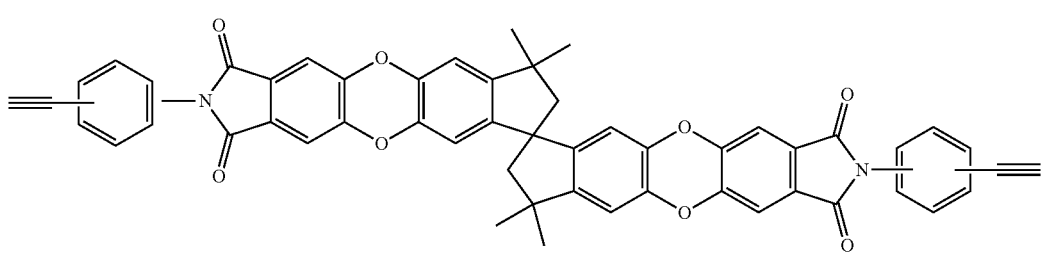

(1F)

The compound for forming an organic film preferably has a terminal structure as described above in view of heat resistance.

In addition, the component (A) preferably satisfies 1.00≤Mw/Mn≤1.10 where Mw is a weight average molecu- Such a material for forming an organic film can be a material for forming an organic film having both higher filling and planarizing properties by the compound for forming an organic film being imparted with thermal flowability with the addition of a high-boiling-point solvent.

The material for forming an organic film preferably further comprises at least one of (C) an acid generator, (D) a surfactant, (E) a crosslinking agent, and (F) a plasticizer.

The inventive material for forming an organic film may contain at least one of the above components (C) to (F) depending on the purpose thereof.

The present invention further provides a substrate for manufacturing a semiconductor device, comprising an organic film on the substrate, the organic film being a cured film of the above-described material for forming an organic film.

The organic film of the present invention has both high filling and planarizing properties, and is therefore an organic film having no fine pores due to insufficient filling or asperity in the organic film surface due to insufficient planarizing. A substrate for manufacturing a semiconductor device planarized by the organic film of the present invention has an increased process margin at patterning, making it possible to manufacture semiconductor devices with high yields.

In addition, the present invention provides a method for forming an organic film employed in a semiconductor device manufacturing process, the method comprising:

spin-coating a substrate to be processed with the above-described material for forming an organic film; and heating the substrate to be processed coated with the material for forming an organic film under an inert gas atmosphere at a temperature of 50° C. or higher to 600° C. or lower for 10 seconds to 7200 seconds to obtain a cured film.

Furthermore, the present invention provides a method for forming an organic film employed in a semiconductor device manufacturing process, the method comprising:

spin-coating a substrate to be processed with the above-described material for forming an organic film;

heating the substrate to be processed coated with the material for forming an organic film in air at a temperature of 50° C. or higher to 250° C. or lower for 5 seconds to 600 seconds to form a coating film; and then performing a heat treatment under an inert gas atmosphere at a temperature of 200° C. or higher to 600° C. or lower for 10 seconds to 7200 seconds to obtain a cured film.

An organic film formed according to the inventive method and employed in a semiconductor device manufacturing process has high heat resistance and high filling and planarizing properties, and allows a favorable semiconductor device yield when used in a semiconductor device manufacturing process.

Furthermore, the inert gas preferably has an oxygen concentration of 1% or less.

The inventive material for forming an organic film is capable of forming an organic film which is sufficiently cured without generating a sublimation product even when the heating is performed under such an inert gas atmosphere, and which also has excellent adhesion to a substrate.

In addition, the substrate to be processed preferably has a structure or a step with a height of 30 nm or more.

The inventive method for forming an organic film is particularly useful when forming a flat organic film on such a substrate to be processed.

In addition, the present invention provides a patterning process comprising:

forming an organic film by using the above-described material for forming an organic film on a body to be processed;

forming a silicon-containing resist middle layer film by using a silicon-containing resist middle layer film material on the organic film;

forming a resist upper layer film by using a photoresist composition on the silicon-containing resist middle layer film;

forming a circuit pattern in the resist upper layer film;

transferring the pattern to the silicon-containing resist middle layer film by etching while using the resist upper layer film having the formed pattern as a mask;

transferring the pattern to the organic film by etching while using the silicon-containing resist middle layer film having the transferred pattern as a mask; and further transferring the pattern to the body to be processed by etching while using the organic film having the transferred pattern as a mask.

Furthermore, the present invention provides a patterning process comprising:

forming an organic film by using the above-described material for forming an organic film on a body to be processed;

forming a silicon-containing resist middle layer film by using a silicon-containing resist middle layer film material on the organic film;

forming an organic antireflective coating on the silicon-containing resist middle layer film;

forming a resist upper layer film by using a photoresist composition on the organic antireflective coating, so that a 4-layered film structure is constructed;

forming a circuit pattern in the resist upper layer film;

transferring the pattern to the organic antireflective coating and the silicon-containing resist middle layer film by etching while using the resist upper layer film having the formed pattern as a mask;

transferring the pattern to the organic film by etching while using the silicon-containing resist middle layer film having the transferred pattern as a mask; and further transferring the pattern to the body to be processed by etching while using the organic film having the transferred pattern as a mask.

In addition, the present invention provides a patterning process comprising:

forming an organic film by using the above-described material for forming an organic film on a body to be processed;

forming an inorganic hard mask selected from a silicon oxide film, a silicon nitride film, a silicon oxynitride film, a titanium oxide film, and a titanium nitride film on the organic film;

forming a resist upper layer film by using a photoresist composition on the inorganic hard mask;

forming a circuit pattern in the resist upper layer film;

transferring the pattern to the inorganic hard mask by etching while using the resist upper layer film having the formed pattern as a mask;

transferring the pattern to the organic film by etching while using the inorganic hard mask having the transferred pattern as a mask; and further transferring the pattern to the body to be processed by etching while using the organic film having the transferred pattern as a mask.

In addition, the present invention provides a patterning process comprising:

forming an organic film by using the above-described material for forming an organic film on a body to be processed;

forming an inorganic hard mask selected from a silicon oxide film, a silicon nitride film, a silicon oxynitride film, a titanium oxide film, and a titanium nitride film on the organic film;

forming an organic antireflective coating on the inorganic hard mask;

forming a resist upper layer film by using a photoresist composition on the organic antireflective coating, so that a 4-layered film structure is constructed;

forming a circuit pattern in the resist upper layer film;

transferring the pattern to the organic antireflective coating and the inorganic hard mask by etching while using the resist upper layer film having the formed pattern as a mask;

transferring the pattern to the organic film by etching while using the inorganic hard mask having the transferred pattern as a mask; and further transferring the pattern to the body to be processed by etching while using the organic film having the transferred pattern as a mask.

The inventive material for forming an organic film can be suitably used for various patterning processes such as a 3-layer resist process using a silicon-containing resist middle layer film or an inorganic hard mask, and a 4-layer resist process additionally using an organic antireflective coating. In a semiconductor device manufacturing process, by forming a circuit pattern according to the inventive patterning process as described, a semiconductor device can be manufactured with a high yield.

In addition, the inorganic hard mask is preferably formed by a CVD method or an ALD method.

In the inventive patterning process, the inorganic hard mask can be formed by such a method, for example.

Furthermore, the circuit pattern is preferably formed by a lithography using light with a wavelength of 10 nm or more to 300 nm or less, a direct drawing by electron beam, a nanoimprinting, or a combination thereof.

In addition, when the circuit pattern is formed, the circuit pattern is preferably developed by alkaline development or with an organic solvent.

In the inventive patterning process, such circuit pattern formation means and development means can be suitably used.

Furthermore, the body to be processed is preferably a semiconductor device substrate or the semiconductor device substrate coated with any of a metal film, a metal carbide film, a metal oxide film, a metal nitride film, a metal oxycarbide film, and a metal oxynitride film.

Furthermore, as the body to be processed, a body to be processed comprising silicon, titanium, tungsten, hafnium, zirconium, chromium, germanium, copper, silver, gold, aluminum, indium, gallium, arsenic, palladium, iron, tantalum, iridium, cobalt, manganese, molybdenum, or an alloy thereof is preferably used.

The inventive patterning process is capable of processing the body to be processed as described above to form a pattern.

In addition, the present invention provides a compound for forming an organic film shown by the following general formula (1A),

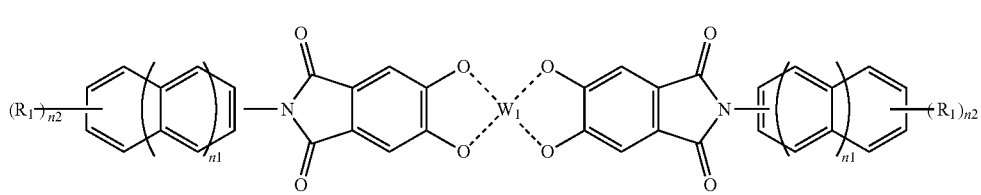

(1A)

wherein $W_1$ represents a tetravalent organic group, n1 represents an integer of 0 or 1, n2 represents an integer of 1 to 3, and $R_1$ represents any one or more of the following general formulae (1B).

(1B)

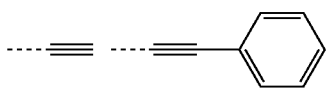

A compound having such an imide structure is cured under film formation conditions of inert gas as well as air, and has high heat resistance and high filling and planarizing properties. Moreover, by combining an imide structure and a heterocyclic structure containing an oxygen functional group, it is possible to achieve a compound for forming an organic film with which an organic film excellent in adhesiveness to a substrate can be formed.

Furthermore, the compound for forming an organic film is preferably shown by the following general formula (1C) or (1D),

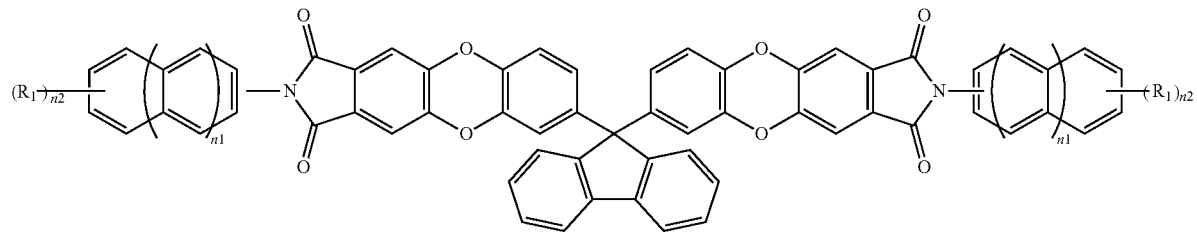

(1C)

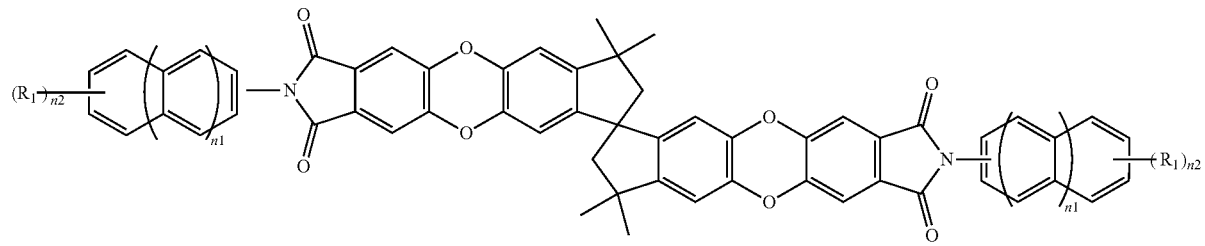

(1D)

wherein n1, n2, and $R_1$ in the formulae have the same meanings as defined above.

Such a compound can provide excellent solvent solubility without losing heat resistance and filling and planarizing properties, and is also a compound for forming an organic film excellent in film formation regardless of the shape of the substrate to be processed.

In addition, the compound for forming an organic film is preferably shown by the following general formula (1E) or (1F).

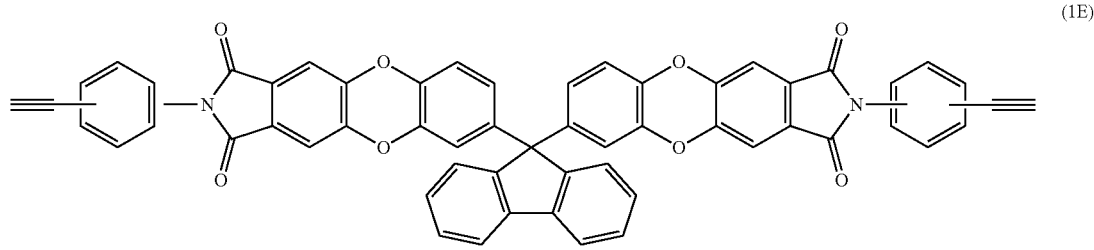

(1E)

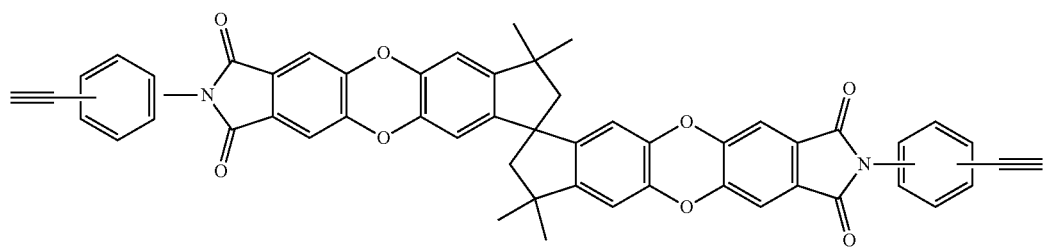

(1F)

Such a compound is a compound for forming an organic film that exhibits excellent heat resistance under baking conditions of either air or inert gas.

Advantageous Effects of Invention

As described above, the inventive compound for forming an organic film is a compound useful for forming an organic film which is cured without generating a by-product even in film formation in an inert gas in which substrate corrosion is prevented, and also has high filling and planarizing properties. Moreover, a material for forming an organic film containing this compound is a material which forms an organic film having excellent filling and planarizing properties, and also having characteristics such as heat resistance, etching resistance, and adhesiveness to a substrate. Accordingly, the inventive material for forming an organic film is extremely useful as, for example, an organic film material in a multilayer resist method such as a 2-layer resist method, a 3-layer resist method using a silicon-containing resist middle layer film, and a 4-layer resist method using a silicon-containing resist middle layer film and an organic antireflective coating, or as a planarizing material for manufacturing a semiconductor device. Moreover, an organic film formed from the inventive material for forming an organic film has excellent heat resistance, and therefore, is suitable for patterning since there is no fluctuation in film thickness due to thermal decomposition even when a CVD hard mask is formed on the organic film.

BRIEF DESCRIPTION OF DRAWINGS

FIG. 1 is an explanatory diagram of the planarizing property in the present invention.

FIG. 2 is an explanatory diagram of an example of an inventive patterning process according to a 3-layer resist method.

FIG. 3 is an explanatory diagram of a method for evaluating the filling property in Examples.

FIG. 4 is an explanatory diagram of a method for evaluating the planarizing property in Examples.

FIG. 5 is an explanatory diagram of a method for measuring the adhesiveness in Examples.

DESCRIPTION OF EMBODIMENTS

As described above, it has been desired to develop a material for forming an organic film, which generates no by-product under such a film formation condition in an inert gas as to prevent substrate corrosion, for example, even at 300° C. or higher, and which is capable of forming an organic film not only excellent in properties of filling and planarizing a pattern formed on a substrate but also favorable for dry-etching resistance during substrate processing. In addition, it has been desired to develop a material for forming an organic film, which causes no fluctuation in film thickness of the organic film due to thermal decomposition even when a CVD hard mask is formed on the organic film; and a compound for forming an organic film useful in a patterning process using the material.

Generally, an organic film is formed as follows. A composition is formed by dissolving a compound for forming an organic film in an organic solvent. Then, a substrate on which a structure, wiring, and so forth of a semiconductor device have been formed is coated with this composition and baked to form the organic film. Immediately after the application of the composition, a coating film is formed along the shape of a step structure on the substrate. Nevertheless, when the coating film is baked, most of the organic solvent is evaporated before curing, so that an organic film is formed from the compound for forming an organic film remaining on the substrate. The present inventors have considered that if the compound for forming an organic film remaining on the substrate has sufficient thermal flowability, the step profile immediately after the application is planarized by thermal flow, and a flat film can be formed.

The present inventors further earnestly studied and consequently found the following. With a compound for forming an organic film having an imide structure shown by the following general formula (1A), the action of a substituent shown by $R_1$ provides thermosetting property equivalent to that of a conventional underlayer film material not only in air but also in inert gas. In addition, adhesiveness, thermal flowability, and high filling and planarizing properties can be provided by a partial structure linked with a dioxin ring. Thus, it is possible to provide a composition for forming an organic film that also has such heat resistance that the composition causes no fluctuation in coating film thickness due to thermal decomposition even when a CVD hard mask is formed. Based on these findings, the present inventors have completed the present invention.

That is, the present invention is a material for forming an organic film, comprising:

(A) a compound for forming an organic film shown by the following general formula (1A); and (B) an organic solvent,

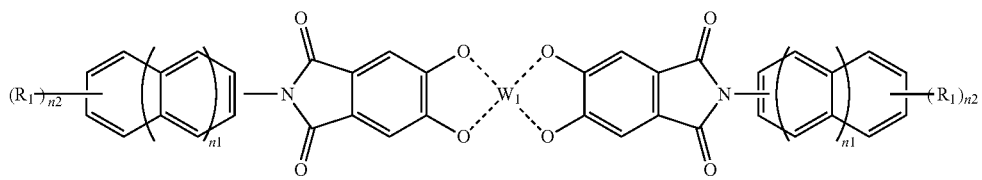

(1A)

wherein $W_1$ represents a tetravalent organic group, n1 represents an integer of 0 or 1, n2 represents an integer of 1 to 3, and $R_1$ represents any one or more of the following general formulae (1B).

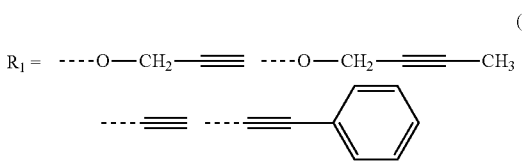

(1B)

Hereinafter, the present invention will be described in detail. However, the present invention is not limited thereto.

<Compound for Forming Organic Film>

The inventive compound for forming an organic film is a compound for forming an organic film shown by the following general formula (1A):

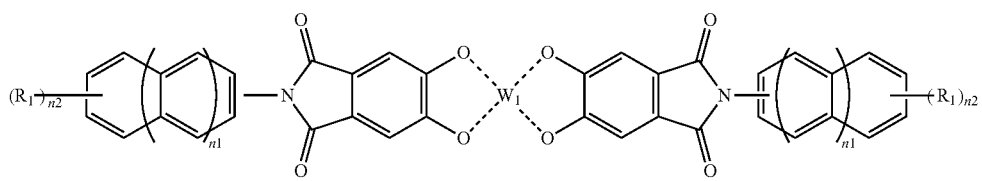

(1A)

where $W_1$ represents a tetravalent organic group, n1 represents an integer of 0 or 1, n2 represents an integer of 1 to 3, and $R_1$ represents any one or more of the following general formulae (1B).

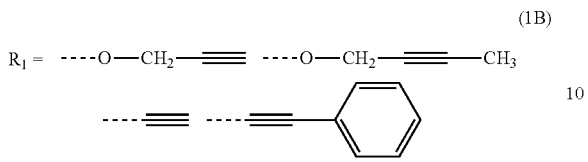

(1B)

An imide compound as in the above (1A) has excellent heat resistance and adhesiveness by the action of an imide group, and it is possible to impart curability in the atmosphere and under an inert gas by the action of a substituent shown by $R_1$. Therefore, an organic film formed using the imide compound of the present invention makes it possible to prevent defects generated due to insufficient heat resistance of the organic film and to prevent film peeling that occurs due to insufficient adhesion when forming an inorganic hard mask on the organic film by a CVD method or an ALD method.

Examples of $W_1$ in the general formula (1A) include the following, and there may be a substituent on the aromatic ring thereof. Examples of the substituent include an alkyl group having 1 to 10 carbon atoms, an alkynyl group and an alkenyl group having 3 to 10 carbon atoms, an aryl group having 6 to 10 carbon atoms, a nitro group, a halogen group, a nitrile group, an alkoxycarbonyl group having 1 to 10 carbon atoms, and an alkanoyloxy group having 1 to 10 carbon atoms. In particular, those having a fluorene ring is preferable from the viewpoint of heat resistance, and those having a spiro ring structure are preferable from the viewpoint of flatness.

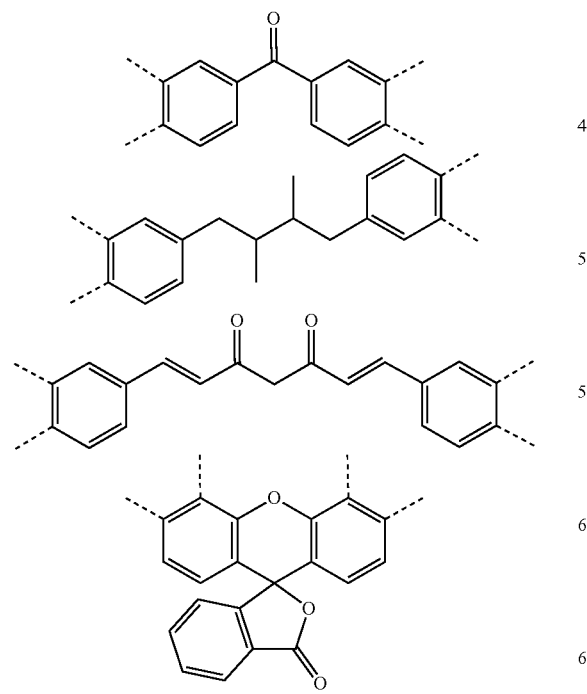

-continued

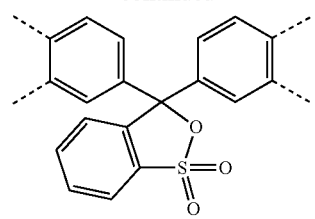

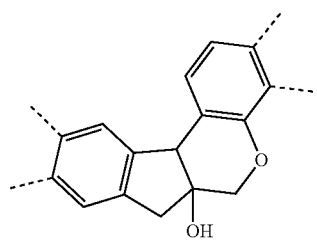

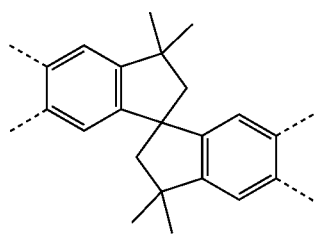

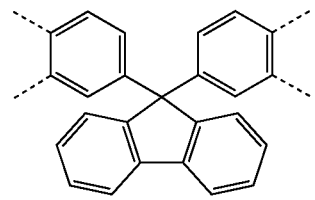

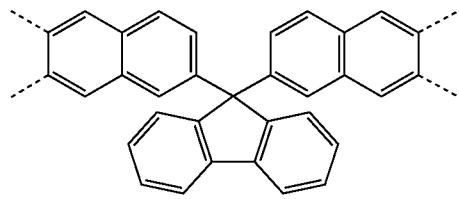

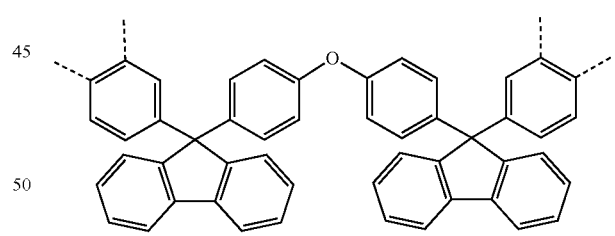

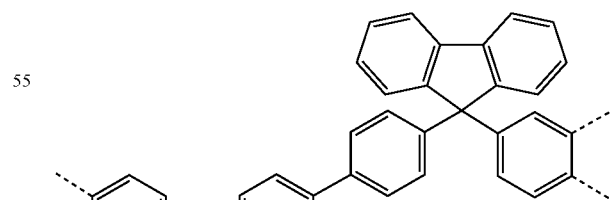

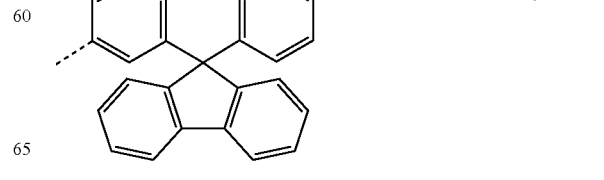

17
-continued

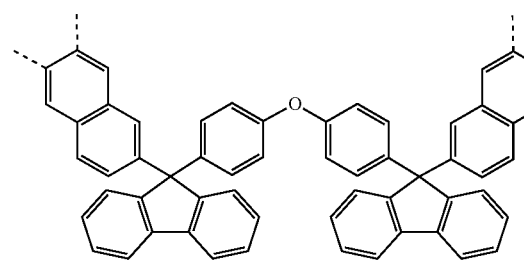

18
-continued

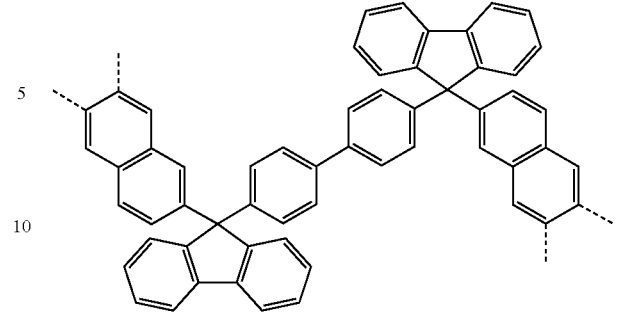

The inventive compound for forming an organic film is preferably a compound having a structure shown by the following general formula (1C) or (1D):

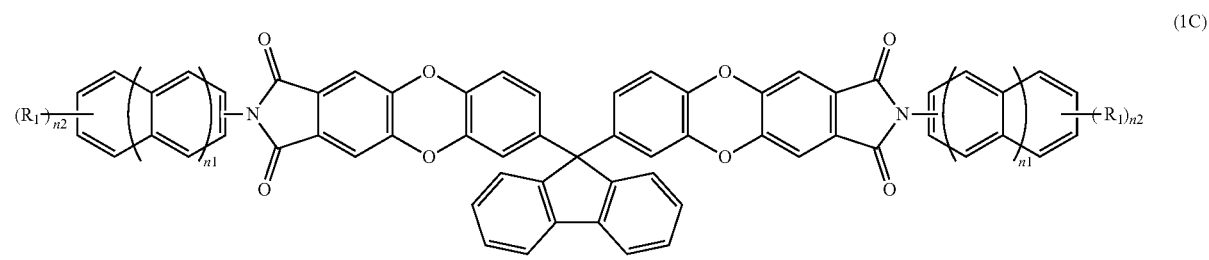

(1C)

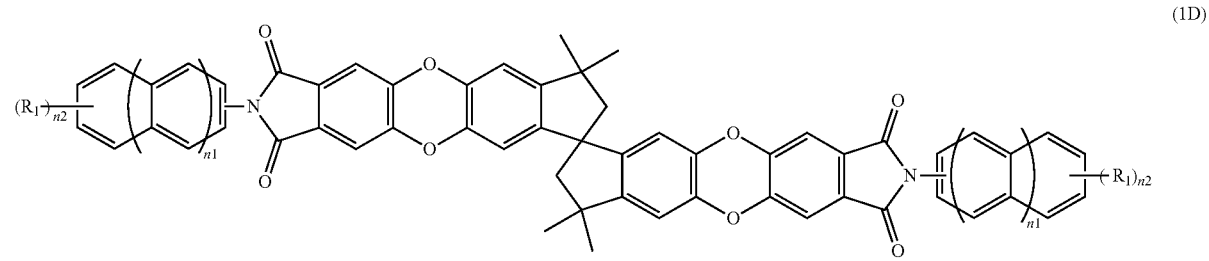

(1D)

where n1, n2, and $R_1$ in the formulae have the same meanings as defined above.

The fluorene structure or spiro structure incorporated in the main skeleton shown by the above (1C) and (1D) make it possible to suppress cohesion of imide rings with each other, impart excellent solubility in an organic solvent, and achieve conflicting properties of heat resistance and filling and planarizing properties.

The inventive compound for forming an organic film is preferably a compound having a structure shown by the following general formula (1E) or (1F):

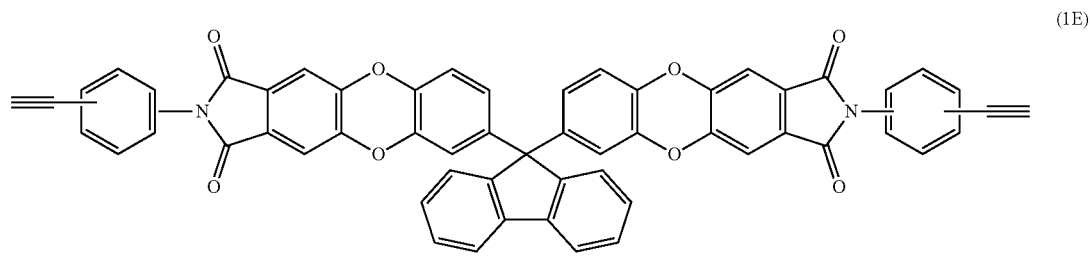

(1E)

-continued (1F)

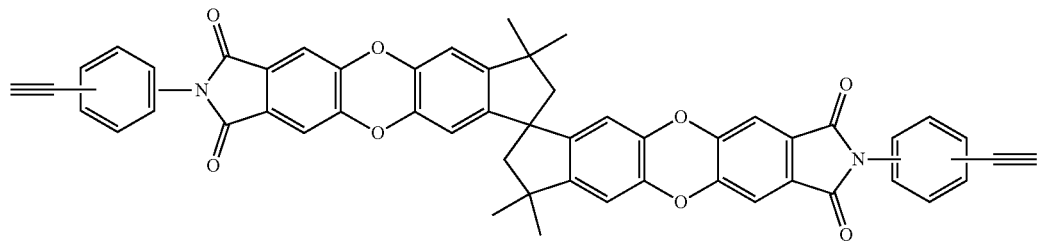

The thermosetting action of an ethynyl group, being a terminal group shown in (1E) and (1F) makes it possible to suppress heat shrinking of a film that occurs when thermosetting an organic film by baking.

The inventive compound for forming an organic film preferably satisfies 1.00≤Mw/Mn≤1.10 where Mw is a weight average molecular weight and Mn is a number average molecular weight measured by gel permeation chromatography in terms of polystyrene.

Controlling Mw/Mn of the compound for forming an organic film within such a range, an organic film excellent in filling property and planarizing property can be formed.

When Mw/Mn is within the above range, thermal flowability of the compound for forming an organic film becomes even more favorable. Therefore, when blended in a composition, the compound can not only favorably fill a fine structure formed on a substrate but also form an organic film making the entire substrate planarized.

[Method for Manufacturing Compound for Forming Organic Film]

As a method for obtaining the inventive compound for forming an organic film, it is possible to synthesize the compound by obtaining an amic acid compound through the reaction of a tetracarboxylic dianhydride and an aniline derivative shown below (STEP 1), followed by thermal or chemical imidization (STEP 2). In this event, in the amic acid compound synthesis, one kind of the tetracarboxylic dianhydride and one kind of the aniline derivative may be used or two or more kinds thereof may be used. These can be appropriately selected and combined according to required properties. $W_1$, $R_1$, n1, and n2 in the following formulae have the same meanings as defined above.

Step 1

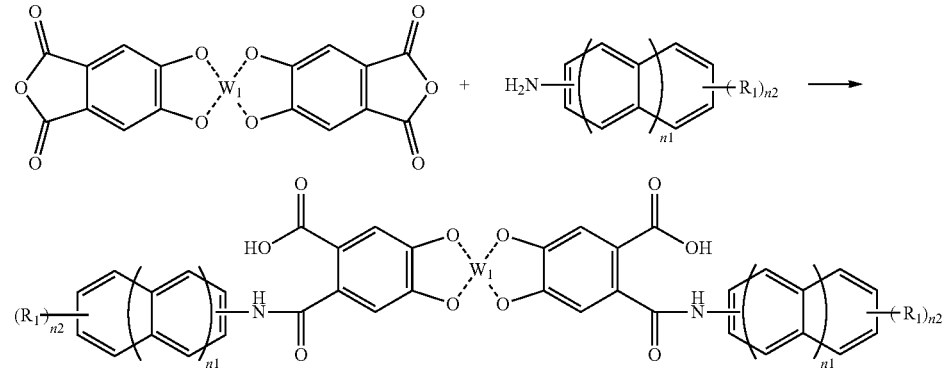

Step 2

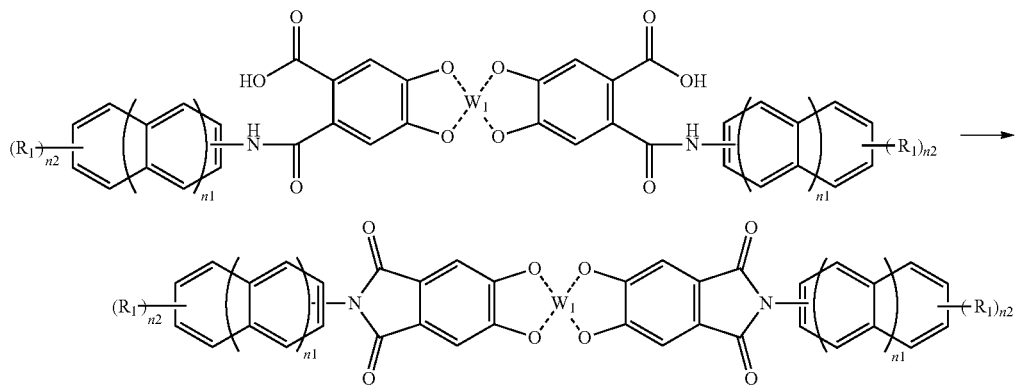

Synthesis of the amic acid shown by STEP 1 can generally be achieved in an organic solvent at room temperature or under cooling or heating as necessary. Examples of the solvent used include alcohols such as methanol, ethanol, isopropyl alcohol, butanol, ethylene glycol, propylene glycol, diethylene glycol, glycerol, ethylene glycol monomethyl ether, propylene glycol monomethyl ether, and propylene glycol monoethyl ether; ethers such as diethyl ether, dibutyl ether, diethylene glycol diethyl ether, diethylene glycol dimethyl ether, tetrahydrofuran, and 1,4-dioxane; chlorinated solvents such as methylene chloride, chloroform, dichloroethane, and trichloroethylene; hydrocarbons such as hexane, heptane, benzene, toluene, xylene, and cumene; nitriles such as acetonitrile; ketones such as acetone, ethyl methyl ketone, isobutyl methyl ketone, and cyclohexanone; esters such as methyl acetate, ethyl acetate, n-butyl acetate, propylene glycol methyl ether acetate, and γ-butyrolactone; non-protic polar solvents such as N-methyl-2-pyrrolidone, N,N-dimethylacetamide, dimethylsulfoxide, N,N-dimethylformamide, and hexamethylphosphoric triamide; and the like. One of these can be used alone or a mixture of two or more thereof can be used. These solvents can be used within a range of 0 to 2,000 parts by mass relative to 100 parts by mass of the reaction raw materials. The reaction temperature is preferably −50° C. to approximately the boiling point of the solvent, and room temperature to 150° C. is even more preferable. Reaction time is appropriately selected from 0.1 to 100 hours.

For these syntheses, a base catalyst can be used as necessary, and examples of the base catalyst include inorganic base compounds such as sodium hydrogen carbonate, sodium carbonate, potassium carbonate, calcium carbonate, cesium carbonate, sodium hydroxide, potassium hydroxide, sodium hydride, and potassium phosphate; organic bases such as triethyl amine, diisopropyl ethyl amine, N,N-dimethylaniline, pyridine, methylpyridine, and 4-dimethylaminopyridine; and the like. One of these or a combination of two or more thereof can be used. The amount used is within the range of 0.01 to 20 moles relative to the number of moles of raw material dianhydride, preferably 0.05 to 10 moles.

The reaction method includes: a method in which the tetracarboxylic dianhydride and the aniline derivative are charged into the solvent at once; a method in which tetracarboxylic dianhydride and aniline derivative separately or mixed are dispersed or dissolved and the resultant is added dropwise to charge; a method in which either the dianhydride or the aniline derivative is dispersed or dissolved in the solvent, then the other dispersed or dissolved in the solvent is added dropwise to charge; and the like. Furthermore, when multiple tetracarboxylic dianhydrides and aniline derivatives are each charged, they can be mixed for reaction beforehand, or they can be made to react individually in succession. When a base catalyst is used, methods include: a method in which the base catalyst is charged at once with the dianhydride or the aniline derivative; a method in which the base catalyst is dispersed or dissolved beforehand, then dropwise addition is performed; and the like. The obtained amic acid solution may proceed successively to the reaction of STEP 2. Furthermore, the obtained amic acid solution may be diluted with an organic solvent, then subjected to liquid-liquid separation and washing to remove unreacted raw materials, the catalyst, and so on present in the system, and thus collected.

The organic solvent used in the liquid-liquid separation and washing is not particularly limited, as long as the organic solvent is capable of dissolving the compounds and is separated into two layers when mixed with water. The organic solvent includes hydrocarbons such as hexane, heptane, benzene, toluene, and xylene; esters such as ethyl acetate, n-butyl acetate, and propylene glycol methyl ether acetate; ketones such as methyl ethyl ketone, methyl amyl ketone, cyclohexanone, and methyl isobutyl ketone; ethers such as diethyl ether, diisopropyl ether, methyl-tert-butyl ether, and ethylcyclopentylmethyl ether; chlorinated solvents such as methylene chloride, chloroform, dichloroethane, and trichloroethylene; mixtures thereof; and the like. As washing water used in this event, generally, what is called deionized water or ultrapure water may be used. The washing may be performed one or more times, preferably approximately one to five times because washing ten times or more does not always produce the full washing effects thereof.

In the liquid-liquid separation and washing, the washing may be performed with a basic aqueous solution to remove the unreacted raw materials or acidic components in the system. The base specifically includes hydroxides of alkaline metals, carbonates of alkaline metals, hydroxides of alkali earth metals, carbonates of alkali earth metals, ammonia, organic ammonium, and the like.

Further, in the liquid-liquid separation and washing, the washing may be performed with an acidic aqueous solution to remove the unreacted raw materials, metal impurities, or basic components in the system. The acid specifically includes inorganic acids such as hydrochloric acid, hydrobromic acid, sulfuric acid, nitric acid, phosphoric acid, and heteropoly acid; organic acids such as oxalic acid, fumaric acid, maleic acid, trifluoroacetic acid, methanesulfonic acid, benzenesulfonic acid, p-toluenesulfonic acid, and trifluoromethanesulfonic acid; and the like.

The liquid-liquid separation and washing may be performed with any one of the basic aqueous solution and the acidic aqueous solution, or can be performed with a combination of the two. The liquid-liquid separation and washing is preferably performed with the basic aqueous solution and the acidic aqueous solution in this order from the viewpoint of removing the metal impurities.

After the liquid-liquid separation and washing with the basic aqueous solution and the acidic aqueous solution, washing with neutral water may be successively performed. The washing may be performed one or more times, preferably approximately one to five times. As the neutral water, deionized water, ultrapure water, or the like as mentioned above may be used. The washing may be performed one or more times, but if the washing is not performed sufficiently, the basic components and acidic components cannot be removed in some cases. The washing is preferably performed approximately one to five times because washing ten times or more does not always produce the full washing effects thereof.

Further, the reaction product after the liquid-liquid separation can also be collected as a powder by concentrating and drying the solvent or crystallizing the reaction product under reduced pressure or normal pressure. Alternatively, the reaction product can also be retained in the state of solution with an appropriate concentration to improve the workability in preparing the material for forming an organic film. The concentration in this event is preferably 0.1 to 50 mass %, more preferably 0.5 to 30 mass %. With such a concentration, the viscosity is hardly increased, making it possible to prevent deterioration of the workability; in addition, since the amount of the solvent is not excessive, it is economical.

The solvent in this event is not particularly limited, as long as the solvent is capable of dissolving the compound.

Specific examples of the solvent include ketones such as cyclohexanone and methyl-2-amyl ketone; alcohols such as 3-methoxybutanol, 3-methyl-3-methoxybutanol, 1-methoxy-2-propanol, and 1-ethoxy-2-propanol; ethers such as propylene glycol monomethyl ether, ethylene glycol monomethyl ether, propylene glycol monoethyl ether, ethylene glycol monoethyl ether, propylene glycol dimethyl ether, and diethylene glycol dimethyl ether; and esters such as propylene glycol monomethyl ether acetate, propylene glycol monoethyl ether acetate, ethyl lactate, ethyl pyruvate, butyl acetate, methyl 3-methoxypropionate, ethyl 3-ethoxy propionate, tert-butyl acetate, tert-butyl propionate, and propylene glycol mono-tert-butyl ether acetate. One of these or a mixture of two or more thereof can be used.

The imidization of the amic acid shown by STEP 2 can be carried out by thermal or chemical imidization. These methods can be suitably selected according to the thermal stability of the linking group in the desired imide compound and the reactivity between the introduced substituent and the reagent used in the chemical imidization.

When a thermal imidization is performed, a solvent capable of forming an azeotrope with water is added to a reaction solution of the amic acid compound obtained in STEP 1, or if collected as a powder, the amic acid compound dissolved in soluble solvent beforehand, and heated to 100° C. to 250° C., and a dehydrative cyclization reaction takes place while generated water is being removed to perform imidization.

As the solvent in this event, it is possible to use esters such as γ-butyrolactone; polar solvents such as N-methyl-2-pyrrolidone, N,N-dimethylacetamide, dimethylsulfoxide, and N,N-dimethylformamide; non-polar solvents such as benzene, toluene, xylene, and mesitylene; and the like. It is preferable to heat one of these solvents or a mixture of two or more thereof, and perform dehydration while distilling the water generated by ring-closure out of the system. These solvents can be used within a range of 0 to 2,000 parts by mass relative to 100 parts by mass of the reaction raw materials.

When a chemical imidization is performed, a base catalyst and an acid anhydride and the like which are a dehydrating agent are added to a reaction solution of the amic acid compound obtained in STEP 1, or if collected as a powder, to the amic acid compound dissolved in soluble solvent beforehand, and heated to 0° C. to 120° C. to perform imidization.

Base catalysts used in the chemical imidization include pyridine, triethyl amine, trimethylamine, tributylamine, trioctylamine, and the like. Among these, pyridine is preferable, having suitable basicity for promoting the reaction. Dehydrating agents include acetic anhydride, trimellitic anhydride, pyromellitic anhydride, trifluoroacetic anhydride, polyphosphoric acid, phosphorus pentoxide, phosphorus pentachloride, and thionyl chloride. Acetic anhydride is preferable from the viewpoint of purification after the reaction. The amount of these catalysts used is within the range of 0.1 to 20 moles relative to the number of moles of raw material dianhydride, preferably 0.2 to 10 moles. Furthermore, as the base catalyst or the dehydrating agent, one of these or a mixture of two or more thereof may be used, and the imidization ratio thereof can be controlled appropriately according to the required performance of the target compound by adjusting the amount of the catalyst, the amount of the dehydrating agent, the reaction temperature, and the reaction time.

The solvent used in this event is not particularly limited, as long as the solvent is inactive in the above reaction.

Examples of the solvent include ethers such as diethylene glycol diethyl ether, diethylene glycol dimethyl ether, tetrahydrofuran, and 1,4-dioxane; chlorinated solvents such as methylene chloride, chloroform, dichloroethane, and trichloroethylene; hydrocarbons such as hexane, heptane, benzene, toluene, xylene, and cumene; nitriles such as acetonitrile; ketones such as acetone, ethyl methyl ketone, isobutyl methyl ketone, and cyclohexanone; esters such as methyl acetate, ethyl acetate, n-butyl acetate, propylene glycol methyl ether acetate, and γ-butyrolactone; non-protic polar solvents such as N-methyl-2-pyrrolidone, N,N-dimethylacetamide, dimethylsulfoxide, N,N-dimethylformamide, and hexamethylphosphoric triamide; and the like. One of these or a mixture of two or more thereof can be used. These solvents can be used within a range of 0 to 2,000 parts by mass relative to 100 parts by mass of the reaction raw materials.

As methods for making these imidized compounds react and collecting the compounds, the methods described in the description of the amic acid compound can be employed.

For the preparation of the amic acid or the imide compound, tetracarboxylic dianhydride and aniline derivative can be combined according to a required performance. Specifically, it is possible to introduce a substituent that contributes to improvement of solvent solubility, adhesion, and filling and planarizing properties, a substituent that contributes to etching resistance and film formation, and the like according to the required performance that is desired. An organic film material using these compounds can achieve both higher filling and planarizing properties as well as higher heat-resistance.

As described above, the inventive compound for forming an organic film gives a composition for forming an organic film having both heat resistance to 400° C. or higher and high filling and planarizing properties.

Note that, in the present invention, the term planarizing property refers to a performance of planarizing the surface of a substrate. For example, as shown in FIG. 1, the composition containing the inventive compound for forming an organic film can reduce a 100-nm step of a substrate 1 to 30 nm or less by coating the substrate 1 with a composition 3' for forming an organic film and heating the resultant to form an organic film 3. Note that the step profile shown in FIG. 1 represents a typical example of the step profile in a substrate for manufacturing a semiconductor device. It is a matter of course that the step profile of a substrate which can be planarized by the composition containing the inventive compound for forming an organic film is not limited thereto.

<Material for Forming Organic Film>

Further, the present invention provides a material for forming an organic film (composition for forming an organic film), containing: (A) the inventive compound for forming an organic film shown by the above-described (1A); and (B) an organic solvent. Note that in the inventive material for forming an organic film, one of the above-described inventive compounds for forming an organic film or a combination of two or more thereof can be used.

The organic solvent that can be used in the inventive material for forming an organic film is not particularly limited as long as the solvent can dissolve the components contained in materials such as the base polymer, an acid generator, a crosslinking agent, and other additives. Specifically, solvents with a boiling point of lower than 180° C. such as those disclosed in paragraphs [0091] and [0092] of JP 2007-199653 A can be used. Above all, propylene glycol monomethyl ether acetate, propylene glycol monomethyl ether, 2-heptanone, cyclopentanone, cyclohexanone, and a mixture of two or more thereof are preferably used.

Such a material for forming an organic film can be applied by spin-coating, and has heat resistance to 400° C. or higher and high filling and planarizing properties because the inventive compound for forming an organic film as described above is incorporated.

Further, the inventive material for forming an organic film may use the organic solvent in which a high-boiling-point solvent having a boiling point of 180° C. or higher is added to the aforementioned solvent having a boiling point of lower than 180° C. (a mixture of the solvent having a boiling point of lower than 180° C. and the solvent having a boiling point of 180° C. or higher). The high-boiling-point organic solvent is not particularly limited to hydrocarbons, alcohols, ketones, esters, ethers, chlorinated solvents, and so forth as long as the high-boiling-point organic solvent is capable of dissolving the compound for forming an organic film. Specific examples of the high-boiling-point organic solvent include 1-octanol, 2-ethylhexanol, 1-nonanol, 1-decanol, 1-undecanol, ethylene glycol, 1,2-propylene glycol, 1,3-butylene glycol, 2,4-pentanediol, 2-methyl-2,4-pentanediol, 2,5-hexanediol, 2,4-heptanediol, 2-ethyl-1,3-hexanediol, diethylene glycol, dipropylene glycol, triethylene glycol, tripropylene glycol, glycerin, n-nonyl acetate, ethylene glycol monohexyl ether, ethylene glycol mono-2-ethylhexyl ether, ethylene glycol monophenyl ether, ethylene glycol monobenzyl ether, diethylene glycol monoethyl ether, diethylene glycol monoisopropyl ether, diethylene glycol mono-n-butyl ether, diethylene glycol monoisobutyl ether, diethylene glycol monohexyl ether, diethylene glycol monophenyl ether, diethylene glycol monobenzyl ether, diethylene glycol diethyl ether, diethylene glycol dibutyl ether, diethylene glycol butylmethyl ether, triethylene glycol dimethyl ether, triethylene glycol monomethyl ether, triethylene glycol-n-butyl ether, triethylene glycol butylmethyl ether, triethylene glycol diacetate, tetraethylene glycol dimethyl ether, dipropylene glycol monomethyl ether, dipropylene glycol mono-n-propyl ether, dipropylene glycol mono-n-butyl ether, tripropylene glycol dimethyl ether, tripropylene glycol monomethyl ether, tripropylene glycol mono-n-propyl ether, tripropylene glycol mono-n-butyl ether, ethylene glycol monoethyl ether acetate, ethylene glycol monobutyl ether acetate, diethylene glycol monomethyl ether acetate, diethylene glycol monoethyl ether acetate, diethylene glycol monobutyl ether acetate, triacetin, propylene glycol diacetate, dipropylene glycol monomethyl ether acetate, dipropylene glycol methyl-n-propyl ether, dipropylene glycol methyl ether acetate, 1,4-butanediol diacetate, 1,3-butylene glycol diacetate, 1,6-hexanediol diacetate, triethylene glycol diacetate, γ-butyrolactone, dihexyl malonate, diethyl succinate, dipropyl succinate, succinate dibutyl, succinate dihexyl, dimethyl adipate, diethyl adipate, dibutyl adipate, and the like. One of these or a mixture thereof may be used.

The boiling point of the high-boiling-point solvent may be appropriately selected according to the temperature at which the material for forming an organic film is heated. The boiling point of the high-boiling-point solvent to be added is preferably 180° C. to 300° C., more preferably 200° C. to 300° C. Such a boiling point prevents the evaporation rate at baking (heating) from becoming excessive, which would otherwise occur if the boiling point is too low. Thus, sufficient thermal flowability can be achieved. Meanwhile, with such a boiling point, the boiling point is not too high, so that the high-boiling-point solvent evaporates after baking and does not remain in the film; thus, the boiling point of 300° C. or lower does not adversely affect the film physical properties such as etching resistance.

When the high-boiling-point solvent is used, the formulation amount of the high-boiling-point solvent is preferably 1 to 30 parts by mass based on 100 parts by mass of the solvent having a boiling point of lower than 180° C. The formulation amount in this range prevents a failure in providing sufficient thermal flowability during baking, which would otherwise occur if the formulation amount is too small. In addition, deterioration of the film physical properties such as etching resistance is prevented, which would otherwise occur if the formulation amount is so large that the solvent remains in the film.

With such a material for forming an organic film, the above-described compound for forming an organic film is provided with thermal flowability by adding the high-boiling-point solvent, so that the material for forming an organic film also has high filling and planarizing properties.

In the inventive material for forming an organic film, (C) an acid generator can be added so as to further promote the curing reaction. The acid generator includes a material that generates an acid by thermal decomposition, and a material that generates an acid by light irradiation. Any acid generator can be added. Specifically, materials disclosed in paragraphs [0061] to [0085] of JP 2007-199653 A can be added, but the present invention is not limited thereto.

One of the acid generators or a combination of two or more thereof can be used. When the acid generator is added, the added amount is preferably 0.05 to 50 parts, more preferably 0.1 to 10 parts, based on 100 parts of the above-described compound.

To the inventive material for forming an organic film, (D) a surfactant can be added so as to enhance the coating property in spin-coating. As the surfactant, for example, those disclosed in [0142] to [0147] of JP 2009-269953 A can be used. When the surfactant is added, the added amount is preferably 0.01 to 10 parts, more preferably 0.05 to 5 parts, based on 100 parts of the above-described compound.

Moreover, to the inventive material for forming an organic film, (E) a crosslinking agent can also be added so as to increase the curability and to further suppress intermixing with an upper layer film. The crosslinking agent is not particularly limited, and known various types of crosslinking agents can be widely used. Examples thereof include melamine-based crosslinking agents, glycoluril-based crosslinking agents, benzoguanamine-based crosslinking agents, urea-based crosslinking agents, p-hydroxyalkylamide-based crosslinking agents, isocyanurate-based crosslinking agents, aziridine-based crosslinking agents, oxazoline-based crosslinking agents, and epoxy-based crosslinking agents.

Specific examples of the melamine-based crosslinking agents include hexamethoxymethylated melamine, hexabutoxymethylated melamine, alkoxy- and/or hydroxy-substituted derivatives thereof, and partial self-condensates thereof. Specific examples of the glycoluril-based crosslinking agents include tetramethoxymethylated glycoluril, tetrabutoxymethylated glycoluril, alkoxy- and/or hydroxy-substituted derivatives thereof, and partial self-condensates thereof. Specific examples of the benzoguanamine-based crosslinking agents include tetramethoxymethylated benzoguanamine, tetrabutoxymethylated benzoguanamine, alkoxy- and/or hydroxy-substituted derivatives thereof, and partial self-condensates thereof. Specific examples of the urea-based crosslinking agents include dimethoxymethylated dimethoxyethyleneurea, alkoxy- and/or hydroxy-substituted derivatives thereof, and partial self-condensates thereof. A specific example of the p-hydroxyalkylamidebased crosslinking agents includes N,N,N',N'-tetra(2-hydroxyethyl)adipic acid amide. Specific examples of the isocyanurate-based crosslinking agents include triglycidyl isocyanurate and triallyl isocyanurate. Specific examples of the aziridine-based crosslinking agents include 4,4'-bis(ethyleneiminocarbonylamino)diphenylmethane and 2,2-bishydroxymethylbutanol-tris[3-(1-aziridinyl)propionate]Specific examples of the oxazoline-based crosslinking agents include 2,2'-isopropylidene bis(4-benzyl-2-oxazoline), 2,2'-isopropylidene bis(4-phenyl-2-oxazoline), 2,2'-methylenebis4,5-diphenyl-2-oxazoline, 2,2'-methylenebis-4-phenyl-2-oxazoline, 2,2'-methylenebis-4-tert-butyl-2-oxazoline, 2,2'-bis(2-oxazoline), 1,3-phenylenebis(2-oxazoline), 1,4-phenylenebis(2-oxazoline), and a 2-isopropenyloxazoline copolymer. Specific examples of the epoxy-based crosslinking agents include diglycidyl ether, ethylene glycol diglycidyl ether, 1,4-butanediol diglycidyl ether, 1,4-cyclohexanedimethanol diglycidyl ether, poly(glycidyl methacrylate), trimethylolethane triglycidyl ether, trimethylolpropane triglycidyl ether, and pentaerythritol tetraglycidyl ether. When the crosslinking agent is added, the added amount is preferably 1 to 100 parts, more preferably 5 to 50 parts based on 100 parts of the above-described compound.

Further, to the inventive material for forming an organic film, (F) a plasticizer can be added so as to further enhance the planarizing and filling properties. The plasticizer is not particularly limited, and known various types of plasticizers can be widely used. Examples thereof include low-molecular-weight compounds such as phthalic acid esters, adipic acid esters, phosphoric acid esters, trimellitic acid esters, and citric acid esters; and polymers such as polyethers, polyesters, and polyacetal-based polymers disclosed in JP 2013-253227 A. When the plasticizer is added, the added amount is preferably 1 to 100 parts, more preferably 5 to 30 parts based on 100 parts of the above-described compound.

Particularly, like the plasticizer, as an additive for providing the inventive material for forming an organic film with filling and planarizing properties, it is preferable to use, for example, liquid additives having polyethylene glycol or polypropylene glycol structures, or thermo-decomposable polymers having a weight loss ratio between 30° C. and 250° C. of 40 mass % or more and a weight average molecular weight of 300 to 200,000. The thermo-decomposable polymers preferably contain a repeating unit having an acetal structure shown by the following general formula (DP1) or (DP1a).

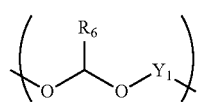

(DP1)

In the formula, $R_6$ represents a hydrogen atom or a saturated or unsaturated monovalent organic group having 1 to 30 carbon atoms which may be substituted. Yi represents a saturated or unsaturated divalent organic group having 2 to 30 carbon atoms.

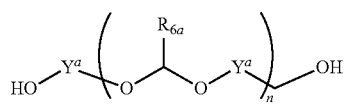

(DP1a)

In the formula, $R_{6a}$ represents an alkyl group having 1 to 4 carbon atoms. $Y^a$ represents a saturated or unsaturated divalent hydrocarbon group having 4 to 10 carbon atoms which may have an ether bond. "n" represents an average repeating unit number of 3 to 500.

As described above, the inventive material for forming an organic film has both heat resistance to 400° C. or higher and high filling and planarizing properties. Thus, the inventive material for forming an organic film is extremely useful as a material for forming an organic film in multilayer resist methods such as a 2-layer resist method, a 3-layer resist method using a silicon-containing resist middle layer film or a silicon-containing inorganic hard mask, and a 4-layer resist method using a silicon-containing resist middle layer film or a silicon-containing inorganic hard mask and an organic antireflective coating. Moreover, the inventive material for forming an organic film generates no by-product even during film formation in an inert gas, and has excellent filling and planarizing properties. Accordingly, the inventive material for forming an organic film can also be suitably used as a planarizing material in a semiconductor device manufacturing process, besides the multilayer resist methods.

<Substrate for Manufacturing Semiconductor Device>

Additionally, the present invention provides a substrate for manufacturing a semiconductor device, including an organic film formed on the substrate, the organic film being formed by curing the above-described material for forming an organic film.

An organic film formed with the inventive material for forming an organic film has both high filling and planarizing properties, and is therefore an organic film having no fine pores due to insufficient filling or asperity in the organic film surface due to insufficient planarizing. Thus, a substrate for a semiconductor device planarized with such an organic film has an increased process margin at patterning, making it possible to manufacture semiconductor devices with high yields.

<Method for Forming Organic Film>

The film formation step by heating to form an organic film (organic underlayer film) can employ 1-stage baking, 2-stage baking, or multi-stage baking of three or more stages. Nevertheless, the 1-stage baking or the 2-stage baking is economically preferable. The film formation by the 1-stage baking is preferably performed at a temperature of 50° C. or higher to 600° C. or lower for 10 to 7200 seconds, preferably at a temperature of 150° C. or higher to 500° C. or lower for 10 to 3600 seconds. Heating under such conditions can promote the planarization attributable to thermal flow and the crosslinking reaction. In a multilayer resist method, a coating-type silicon-containing resist middle layer film or a CVD hard mask is sometimes formed on a film thus obtained. In the case where a coating-type silicon-containing resist middle layer film is employed, the film formation is performed preferably at a temperature higher than a temperature at which the silicon-containing resist middle layer film is formed. Generally, a silicon-containing resist middle layer film is formed at 100° C. or higher to 400° C. or lower, preferably 150° C. or higher to 350° C. or lower. Forming the organic film at a temperature higher than these temperatures makes it possible to prevent a composition for forming a silicon-containing resist middle layer film from dissolving the organic film, and to form an organic film not mixed with the composition.

In the case where a CVD hard mask is employed, the organic film is formed preferably at a temperature higher than a temperature at which the CVD hard mask is formed.

Examples of the temperature at which the CVD hard mask is formed include temperatures at 150° C. or higher to 500° C. or lower.

On the other hand, in film formation by the 2-stage baking, a first baking is performed in air with a temperature having an upper limit of 300° C. or lower, preferably 250° C. or lower for 5 to 600 seconds, considering the influence of substrate corrosion due to oxygen in air. The second baking temperature is higher than the first baking temperature, and the second baking is preferably performed at a temperature of 600° C. or lower, preferably 500° C. or lower, for preferably 10 to 7200 seconds. In a multilayer resist method, a coating-type silicon-containing resist middle layer film or a CVD hard mask is sometimes formed on a film thus obtained. In the case where a coating-type silicon-containing resist middle layer film is employed, the film formation is performed preferably at a temperature higher than a temperature at which the silicon-containing resist middle layer film is formed. Generally, a silicon-containing resist middle layer film is formed at 100° C. or higher to 400° C. or lower, preferably 150° C. or higher to 350° C. or lower. Forming the organic film at a temperature higher than these temperatures makes it possible to prevent a composition for forming a silicon-containing resist middle layer film from dissolving the organic film, and to form an organic film not mixed with the composition.

In the case where a CVD hard mask is employed in the 2-stage baking, the organic film is formed preferably at a temperature higher than a temperature at which the CVD hard mask is formed. Examples of the temperature at which the CVD hard mask is formed include temperatures at 150° C. or higher to 500° C. or lower.

In addition, the present invention provides a method for forming an organic film that functions as an organic underlayer film used in a semiconductor device manufacturing process where a cured film is formed by heating a substrate to be processed in an atmosphere with an oxygen concentration of 1% or less to prevent corrosion of the substrate to be processed.

In this method for forming an organic film, first of all, a substrate to be processed is spin-coated with the above-described inventive material for forming an organic film. After the spin-coating, in the 2-stage baking, first, baking is performed in air at 300° C. or lower. Then, the second baking is performed under an atmosphere with an oxygen concentration of 1% or less. In the 1-stage baking, the first baking in air can be skipped. Note that examples of the atmosphere during the baking include such inert gases as nitrogen, argon, and helium. The inventive material for forming an organic film is capable of forming a sufficiently cured organic film without generating a sublimation product, even when the baking is performed under such an inert gas atmosphere.

Meanwhile, the inventive methods for forming an organic film make it possible to use a substrate to be processed having a structure or a step with a height of 30 nm or more. As described above, since the inventive material for forming an organic film is excellent in filling and planarizing properties, even when the substrate to be processed has a structure or a step (asperity) with a height of 30 nm or more, a flat cured film can be formed. That is, the inventive method for forming an organic film is particularly useful when a flat organic film is formed on such a substrate to be processed.

Note that the thickness of the organic film to be formed is appropriately selected, but is preferably 30 to 20,000 nm, particularly preferably 50 to 15,000 nm.

Additionally, the above-described methods for forming an organic film are applicable, using the inventive material for forming an organic film, to both cases where an organic film for an organic underlayer film is formed, and where an organic film for a flat film is formed.

The present invention provides a method for forming an organic film employed in a semiconductor device manufacturing process, the method including:

spin-coating a substrate to be processed with the above-described material for forming an organic film; and heating the substrate to be processed coated with the material for forming an organic film under an inert gas atmosphere at a temperature of 50° C. or higher to 600° C. or lower for 10 seconds to 7200 seconds to obtain a cured film.

In addition, the present invention provides a method for forming an organic film that can planarize the surface of a stepped substrate used in a semiconductor device manufacturing process, the method including:

spin-coating a substrate to be processed with the above-described inventive material for forming an organic film;

heating the substrate coated with the material for forming an organic film in air at a temperature of 50° C. or higher to 250° C. or lower for 10 to 600 seconds; and then performing a heat treatment in an inert gas at a temperature of 200° C. or higher to 600° C. or lower, preferably at a temperature of 250° C. or higher for 10 to 7200 seconds to form a cured film.

In these methods for forming an organic film, first, a substrate to be processed is spin-coated with the above-described inventive material for forming an organic film. By employing the spin-coating method, favorable filling property can be obtained. After the spin-coating, baking (heating) is performed to promote the planarization attributable to thermal flow and the crosslinking reaction. Note that since this baking allows the solvent in the material for forming an organic film to evaporate, even when a resist upper layer film or a silicon-containing resist middle layer film is formed on the organic film, the mixing can be prevented.

<Patterning Processes>

[3-Layer Resist Method Using Silicon-Containing Resist Middle Layer Film]

The present invention provides a patterning process including:

forming an organic film by using the above-described inventive material for forming an organic film on a body to be processed;

forming a silicon-containing resist middle layer film by using a silicon-containing resist middle layer film material containing a silicon atom on the organic film;

forming a resist upper layer film by using a resist upper layer film material containing a photoresist composition on the silicon-containing resist middle layer film;

forming a circuit pattern in the resist upper layer film;

transferring the pattern to the silicon-containing resist middle layer film by etching while using the resist upper layer film having the formed circuit pattern as a mask;

transferring the pattern to the organic film by etching while using the silicon-containing resist middle layer film having the transferred pattern as a mask; and further transferring the pattern to the body to be processed by etching while using the organic film having the transferred pattern as a mask.

As the body to be processed, it is preferable to use a semiconductor device substrate or the semiconductor device substrate coated with any of a metal film, a metal carbide film, a metal oxide film, a metal nitride film, a metal oxycarbide film, and a metal oxynitride film. More specifically, examples of the body which may be used include, but are not particularly limited to: substrates made of Si, α-Si, p-Si, SiO$_2$, SiN, SiON, W, TiN, Al, or the like; and these substrates coated with the above-described metal film or the like as a layer to be processed.

As the layer to be processed, used are various Low-k films made of Si, SiO$_2$, SiON, SiN, p-Si, α-Si, W, W—Si, Al, Cu, Al—Si, or the like, and stopper films thereof. The layer can be formed to have a thickness of generally 50 to 10,000 nm, particularly 100 to 5,000 nm. Note that when the layer to be processed is formed, the substrate and the layer to be processed are formed from different materials.

Note that the body to be processed used preferably contains silicon, titanium, tungsten, hafnium, zirconium, chromium, germanium, copper, silver, gold, aluminum, indium, gallium, arsenic, palladium, iron, tantalum, iridium, cobalt, manganese, molybdenum, or an alloy thereof.

Further, as the body to be processed, a substrate to be processed having a structure or a step with a height of 30 nm or more is preferably used.

When the organic film is formed on the body to be processed using the inventive material for forming an organic film, the above-described inventive methods for forming an organic film can be employed.

Next, using a resist middle layer film material containing silicon atoms, a resist middle layer film (silicon-containing resist middle layer film) is formed on the organic film. The silicon-containing resist middle layer film material is preferably a polysiloxane-based middle layer film material. The silicon-containing resist middle layer film having an antireflective effect can suppress the reflection. Particularly, for 193-nm light exposure, a material containing many aromatic groups and having a high etching selectivity relative to the substrate is used as a material for forming an organic film, so that the k-value and thus the substrate reflection are increased; in contrast, the reflection can be suppressed by imparting absorption to the silicon-containing resist middle layer film so as to have an appropriate k-value, and the substrate reflection can be reduced to 0.5% or less. As the silicon-containing resist middle layer film having an antireflective effect, a polysiloxane is preferably used which has anthracene for 248-nm and 157-nm light exposure, or a phenyl group or a light-absorbing group having a silicon-silicon bond for 193-nm light exposure in a pendant structure or a polysiloxane structure, and which is crosslinked by an acid or heat.

Next, using a resist upper layer film material composed of a photoresist composition, a resist upper layer film is formed on the silicon-containing resist middle layer film. The resist upper layer film material may be a positive type or a negative type, and any generally-used photoresist composition can be used. After the spin-coating of the resist upper layer film material, pre-baking is preferably performed at 60 to 180° C. for 10 to 300 seconds. Then, light exposure, and furthermore, post-exposure bake (PEB), and development are performed according to conventional methods to obtain a resist upper layer film pattern. Note that the thickness of the resist upper layer film is not particularly limited, but is preferably 30 to 500 nm, particularly preferably 50 to 400 nm.

Next, a circuit pattern (the resist upper layer film pattern) is formed in the resist upper layer film. The circuit pattern is preferably formed by a lithography using light with a wavelength ranging from 10 nm or more to 300 nm or less, a direct drawing by electron beam, a nanoimprinting, or a combination thereof.

Note that the exposure light includes high energy beam with a wavelength of 300 nm or less; specifically, deep ultraviolet ray, KrF excimer laser beam (248 nm), ArF excimer laser beam (193 nm), F$_2$ laser beam (157 nm), Kr$_2$ laser beam (146 nm), Ar$_2$ laser beam (126 nm), soft X-ray (EUV) with a wavelength of 3 to 20 nm, electron beam (EB), ion beam, X-ray, and the like.

Furthermore, when the circuit pattern is formed, the circuit pattern is preferably developed by alkaline development or with an organic solvent.

Next, the pattern is transferred to the silicon-containing resist middle layer film by etching while using the resist upper layer film having the formed circuit pattern as a mask. The etching of the silicon-containing resist middle layer film while using the resist upper layer film pattern as a mask is preferably performed with a fluorocarbon-based gas. Thereby, a silicon-containing resist middle layer film pattern is formed.

Next, the pattern is transferred to the organic film by etching while using the silicon-containing resist middle layer film having the transferred pattern as a mask. Since the silicon-containing resist middle layer film exhibits higher etching resistance to an oxygen gas or a hydrogen gas than that of an organic material, the etching of the organic film while using the silicon-containing resist middle layer film pattern as a mask is preferably performed with an etching gas mainly containing an oxygen gas or a hydrogen gas. Thereby, an organic film pattern can be formed.

Next, the pattern is transferred to the body to be processed by etching while using the organic film having the transferred pattern as a mask. The subsequent etching of the body to be processed (layer to be processed) can be performed according to a conventional method. For example, the body to be processed made of SiO$_2$, SiN, or silica low-dielectric insulating film is etched mainly with a fluorocarbon-based gas. The body to be processed made of p-Si, Al, or W is etched mainly with a chlorine- or bromine-based gas. When the substrate is processed by etching with a fluorocarbon-based gas, the silicon-containing resist middle layer film pattern is removed together with the substrate processing. Meanwhile, when the substrate is processed by etching with a chlorine- or bromine-based gas, the silicon-containing resist middle layer film pattern needs to be removed by additional dry-etching with a fluorocarbon-based gas after the substrate processing.

The organic film obtained using the inventive material for forming an organic film can exhibit excellent etching resistance when the body to be processed is etched as described above.

[4-Layer Resist Method Using Silicon-Containing Resist Middle Layer Film and Organic Antireflective Coating]

Furthermore, the present invention provides a patterning process including:

forming an organic film by using the above-described inventive material for forming an organic film on a body to be processed;

forming a silicon-containing resist middle layer film by using a resist middle layer film material containing a silicon atom on the organic film;

forming an organic antireflective coating on the silicon-containing resist middle layer film;

forming a resist upper layer film by using a resist upper layer film material containing a photoresist composition on the organic antireflective coating;

forming a circuit pattern in the resist upper layer film;

transferring the pattern to the organic antireflective coating and the silicon-containing resist middle layer film by dry-etching while using the resist upper layer film having the formed circuit pattern as a mask;

transferring the pattern to the organic film by etching while using the silicon-containing resist middle layer film having the transferred pattern as a mask; and further transferring the pattern to the body to be processed by etching while using the organic film having the transferred pattern as a mask.

Note that this method can be performed in the same manner as the above-described 3-layer resist method using the silicon-containing resist middle layer film, except that the organic antireflective coating (BARC) is formed between the silicon-containing resist middle layer film and the resist upper layer film.

The organic antireflective coating can be formed by spin-coating using a known organic antireflective coating material.

[3-Layer Resist Method Using Inorganic Hard Mask]

Furthermore, as a patterning process by a 3-layer resist method using the above-described inventive material for forming an organic film, the present invention provides a patterning process including:

forming an organic film by using the above-described inventive material for forming an organic film on a body to be processed;

forming an inorganic hard mask selected from a silicon oxide film, a silicon nitride film, a silicon oxynitride film, a titanium oxide film, and a titanium nitride film on the organic film;

forming a resist upper layer film by using a resist upper layer film material including a photoresist composition on the inorganic hard mask;

forming a circuit pattern in the resist upper layer film;

transferring the pattern to the inorganic hard mask by etching while using the resist upper layer film having the formed circuit pattern as a mask;

transferring the pattern to the organic film by etching while using the inorganic hard mask having the transferred pattern as a mask; and further transferring the pattern to the body to be processed by etching while using the organic film having the transferred pattern as a mask.

Note that this method can be performed in the same manner as the above-described 3-layer resist method using the silicon-containing resist middle layer film, except that the inorganic hard mask is formed in place of the silicon-containing resist middle layer film on the organic film.

The inorganic hard mask selected from a silicon oxide film, a silicon nitride film, a silicon oxynitride film (SiON film), a titanium oxide film, and a titanium nitride film can be formed by a CVD method, an ALD method, or the like. The method for forming the silicon nitride film is disclosed in, for example, JP 2002-334869 A, WO 2004/066377 A1, and so forth. The film thickness of the inorganic hard mask is preferably 5 to 200 nm, more preferably 10 to 100 nm. As the inorganic hard mask, a SiON film is most preferably used which is effective as an antireflective coating. When the SiON film is formed, the substrate temperature reaches 300 to 500° C. Hence, the underlayer film needs to withstand the temperature of 300 to 500° C. Since the organic film formed using the composition for forming an organic film of the present invention has high heat-resistance and can withstand high temperatures of 300° C. to 500° C., this enables the combination of the inorganic hard mask formed by a CVD method or an ALD method with the organic film formed by a spin-coating method.

[4-Layer Resist Method Using Inorganic Hard Mask and Organic Antireflective Coating]

Furthermore, as a patterning process by a 4-layer resist method using the above-described inventive material for forming an organic film, the present invention provides a patterning process including:

forming an organic film by using the above-described inventive material for forming an organic film on a body to be processed;

forming an inorganic hard mask selected from a silicon oxide film, a silicon nitride film, a silicon oxynitride film, a titanium oxide film, and a titanium nitride film on the organic film;

forming an organic antireflective coating on the inorganic hard mask;

forming a resist upper layer film by using a resist upper layer film material containing a photoresist composition on the organic antireflective coating;

forming a circuit pattern in the resist upper layer film;

transferring the pattern to the organic antireflective coating and the inorganic hard mask by etching while using the resist upper layer film having the formed circuit pattern as a mask;

transferring the pattern to the organic film by etching while using the inorganic hard mask having the transferred pattern as a mask; and further transferring the pattern to the body to be processed by etching while using the organic film having the transferred pattern as a mask.

Note that this method can be performed in the same manner as the above-described 3-layer resist method using the inorganic hard mask, except that the organic antireflective coating (BARC) is formed between the inorganic hard mask and the resist upper layer film.

Particularly, when the SiON film is used as the inorganic hard mask, two antireflective coatings including the SiON film and the BARC make it possible to suppress the reflection even in liquid immersion exposure at a high NA exceeding 1.0. Another merit of the BARC formation is having an effect of reducing footing of the resist upper layer film pattern immediately above the SiON film.

Herein, FIG. 2 (A) to (F) show an example of the inventive patterning process according to the 3-layer resist method. In the 3-layer resist method, as shown in FIG. 2 (A), using the inventive material for forming an organic film, an organic film 3 is formed on a layer 2 to be processed formed on a substrate 1. Then, a silicon-containing resist middle layer film 4 is formed on the organic film 3, and a resist upper layer film 5 is formed on the silicon-containing resist middle layer film 4. Subsequently, as shown in FIG. 2 (B), a portion 6 to be exposed of the resist upper layer film 5 is exposed to light, followed by PEB (post-exposure bake). Thereafter, as shown in FIG. 2 (C), a resist upper layer film pattern 5a is formed by development. After that, as shown in FIG. 2 (D), using the resist upper layer film pattern 5a as a mask, the silicon-containing resist middle layer film 4 is processed by dry-etching with a fluorocarbon-based gas. Thereby, a silicon-containing resist middle layer film pattern 4a is formed. Then, as shown in FIG. 2 (E), after the resist upper layer film pattern 5a is removed, the organic film 3 is etched with oxygen plasma while using the silicon-containing resist middle layer film pattern 4a as a mask. Thereby, an organic film pattern 3a is formed. Further, as shown in FIG. 2 (F), after the silicon-containing resist middle layer film pattern 4a is removed, the layer 2 to be processed is processed by etching while using the organic film pattern 3a as a mask. Thus, a pattern 2a is formed.

In the case where an inorganic hard mask is formed, the silicon-containing resist middle layer film 4 may be replaced with the inorganic hard mask. In the case where a BARC is formed, the BARC may be formed between the silicon-containing resist middle layer film 4 and the resist upper layer film 5. The BARC may be etched continuously and before the etching of the silicon-containing resist middle layer film 4. Alternatively, after the BARC is etched alone, the silicon-containing resist middle layer film 4 may be etched, for example, after an etching apparatus is changed.

As described above, the inventive patterning processes make it possible to precisely form a fine pattern in a body to be processed by the multilayer resist methods.

EXAMPLE

Hereinafter, the present invention will be more specifically described with reference to Synthesis Examples, Comparative Synthesis Examples, Examples, and Comparative Examples. However, the present invention is not limited thereto. Note that, with respect to molecular weight and dispersity, weight average molecular weight (Mw) and number average molecular weight (Mn) were measured by gel permeation chromatography (GPC) using tetrahydrofuran as an eluent in terms of polystyrene, and dispersity (Mw/Mn) was calculated therefrom.

Synthesis Examples: Synthesis of Compounds for Material for Forming Organic Film Compounds (A1) to (A6) for a material for forming an organic film and comparative compounds (R1) to (R3) were synthesized using tetracarboxylic dianhydrides: (B1) to (B3) and aniline derivatives: (C1) to (C6) shown below.

Tetracarboxylic Dianhydrides:

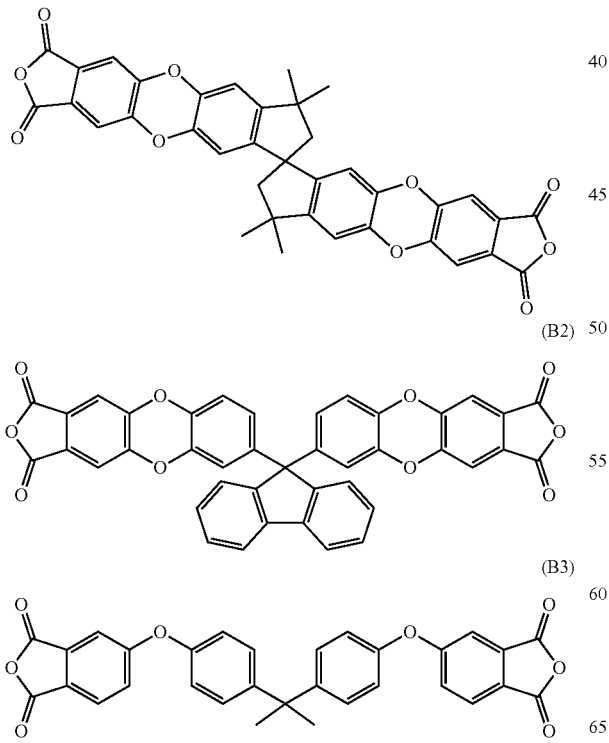

In (B3), a reagent of Tokyo Chemical Industry Co., Ltd. was used.

Aniline Derivatives:

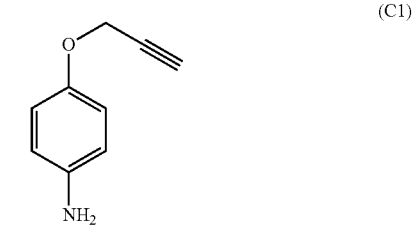

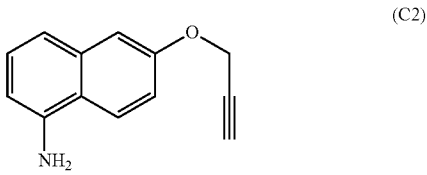

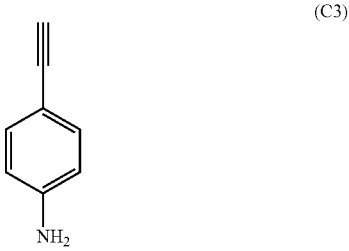

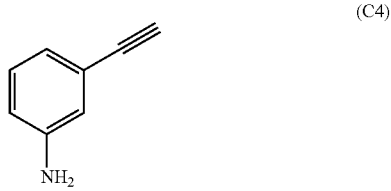

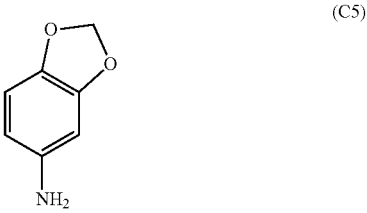

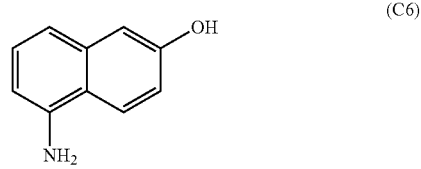

Tetracarboxylic anhydrides (B1) and (B2) were synthesized as follows.

Synthesis of Tetracarboxylic Anhydride (B1) and Synthesis of Intermediate (b1)

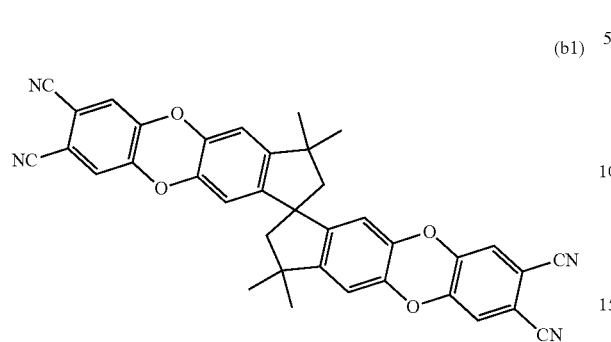

(b1)

A dispersion was formed by adding 100 g of N-methylpyrrolidone (NMP) to 15.61 g of 5,5',6,6'-tetrahydroxy-3,3,3',3'-tetramethyl-1,1'-spirobiindan and 31.68 g of potassium carbonate under a nitrogen atmosphere at an inner temperature of 70° C. Then, 63.2 g of a 25 wt % solution of 4,5-difluorophthalonitrile in NMP was slowly added dropwise. Subsequently, the reaction was allowed to proceed at an inner temperature of 80° C. for 6 hours. After cooling to room temperature, the obtained reaction solution was dropped into 500 g of pure water, and a crystal was precipitated. The precipitated crystal was separated by filtration, washed twice with 300 ml of pure water, twice with 300 ml of methanol, and the crystal was collected. The collected crystal was vacuum dried at 70° C. Thus, 25.89 g of (b1) was obtained.

Synthesis of Tetracarboxylic Anhydride (B1) and Synthesis of Intermediate (b2)

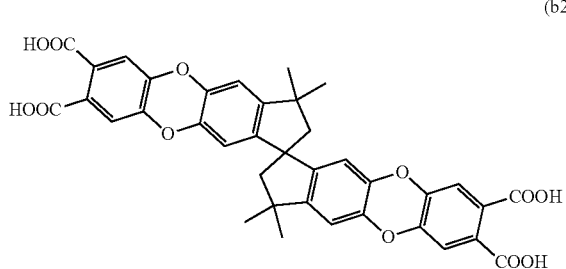

(b2)

50 g of ultrapure water and 50 g of ethanol were added to 20.32 g of (b1) and 13.67 g of KOH, and a reaction was allowed to proceed under a nitrogen atmosphere at an inner temperature of 80° C. for 30 hours. After cooling to room temperature, the obtained reaction solution was dropped into 150 g of a 5% aqueous hydrochloric acid. Then, extraction was carried out with 400 ml of ethyl acetate. The organic layer was collected and further washed four times with 100 ml of pure water. Then, the organic layer was evaporated under reduced pressure to dryness. After a homogeneous solution was formed by adding 100 g of THF to the residue, a crystal was precipitated with 500 g of diisopropyl ether (IPE). The precipitated crystal was separated by filtration, washed twice with 300 ml of IPE, and collected. The collected crystal was vacuum dried at 70° C. Thus, 21.91 g of (b2) was obtained.

Synthesis of Tetracarboxylic Anhydride (B1)

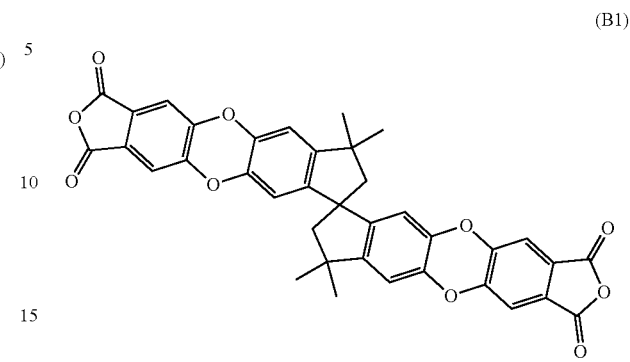

(B1)

160 g of acetic anhydride was added to 21.8 g of (b2), and a reaction was allowed to proceed under a nitrogen atmosphere at an inner temperature of 150° C. After cooling the obtained reaction solution to room temperature, 300 g of toluene was added. The precipitated crystal was separated by filtration, washed three times with 200 ml of toluene, and the crystal was collected. The collected crystal was vacuum dried at 70° C. Thus, 19.00 g of (B1) was obtained.

Synthesis of Tetracarboxylic Anhydride (B2) and Synthesis of Intermediate (b3)

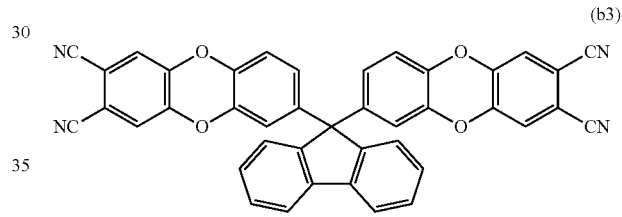

(b3)

A dispersion was formed by adding 100 g of N-methylpyrrolidone (NMP) to 21.04 g of 9,9-bis(3,4-dihydroxyphenyl)fluorene and 36.14 g of potassium carbonate under a nitrogen atmosphere at an inner temperature of 70° C. Then, 75.84 g of a 25 wt % solution of 4,5-difluorophthalonitrile in NMP was slowly added dropwise. Subsequently, the reaction was allowed to proceed at an inner temperature of 80° C. for 6 hours. After cooling to room temperature, 300 ml of toluene and 500 ml of pure water were added to the reaction liquid to dissolve precipitated salt, and then the separated aqueous layer was removed. Further, the organic layer was washed with 100 ml of pure water. Then, 200 ml of methanol was added, and a crystal was precipitated in the organic layer. The precipitated crystal was separated by filtration, washed twice with 300 ml of methanol, and collected. The collected crystal was vacuum dried at 70° C. Thus, 26.32 g of (b3) was obtained.

Synthesis of Tetracarboxylic Anhydride (B2) and Synthesis of Intermediate (b4)

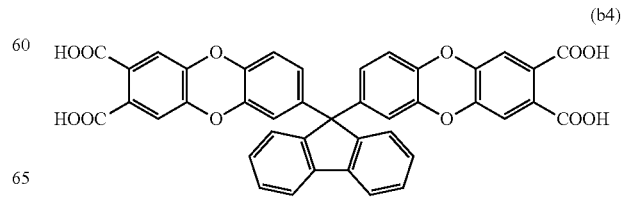

(b4)

100 g of ultrapure water and 100 g of ethanol were added to 26.20 g of (b3) and 21.94 g of KOH, and a reaction was allowed to proceed under a nitrogen atmosphere at an inner temperature of 80° C. for 24 hours. After cooling to room temperature, the obtained reaction solution was dropped into 400 g of a 5% aqueous hydrochloric acid. Then, extraction was carried out with a mixed solvent of 200 ml of ethyl acetate and 200 ml of THF. The collected organic layer was further washed four times with 100 ml of ultrapure water. Subsequently, the organic layer was evaporated under reduced pressure to dryness. After a homogeneous solution was formed by adding 50 g of THE to the residue, 300 g of toluene was added to precipitate a crystal. The precipitated crystal was separated by filtration, washed twice with 300 ml of IPE, and the crystal was collected. The collected crystal was vacuum dried at 70° C. Thus, 28.10 g of (b4) was obtained.

Synthesis of Tetracarboxylic Anhydride (B2)

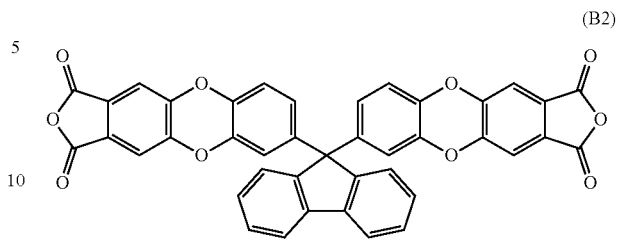

(B2)

160 g of acetic anhydride was added to 28.00 g of (b4), and a reaction was allowed to proceed under a nitrogen atmosphere at an inner temperature of 150° C. After cooling the obtained reaction solution to room temperature, 300 g of toluene was added to precipitate a crystal. The precipitated crystal was separated by filtration, washed twice with 200 ml of toluene, washed with 200 ml of IPE, and the crystal was collected. The collected crystal was vacuum dried at 70° C. Thus, 11.40 g of (B2) was obtained.

[Synthesis Example 1] Synthesis of Compound (A1)

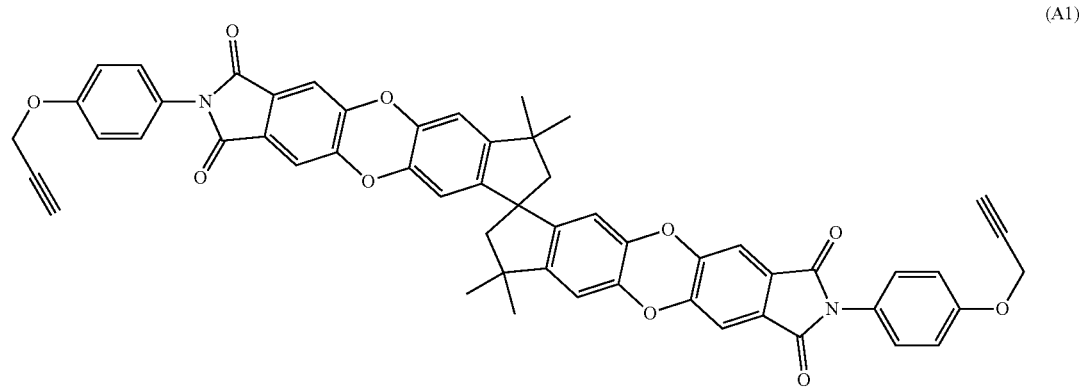 [SMILES: C#CCOc1ccc(-n2c(=O)c3cc4oc5cc6c(cc5oc4cc3c2=O)C2(CC6(C)C)CC(C)(C)c3cc4oc5cc6c(=O)n(-c7ccc(OCC#C)cc7)c(=O)c6cc5oc4cc32)cc1]

(A1)

A homogeneous solution was formed by adding 30 g of N-methylpyrrolidone to 5.0 g of tetracarboxylic anhydride (B1) under a nitrogen atmosphere at an inner temperature of 40° C. Then, 2.46 g of amine compound (C1) was added and the reaction was allowed to proceed at an inner temperature of 40° C. for 3 hours to obtain an amic acid solution. 1.26 g of pyridine was added to the obtained amic acid solution, and 3.25 g of acetic anhydride was further added dropwise slowly. Then, the reaction was allowed to proceed at an inner temperature of 60° C. for 4 hours for imidization. 100 ml of methyl isobutyl ketone and 50 ml of pure water were added to the reaction liquid for homogenization, then the separated aqueous layer was removed. Further, the organic layer was washed six times with 50 ml of a 3% nitric acid aqueous solution and 50 ml of pure water. Then, the organic layer was evaporated under reduced pressure to dryness. After a homogeneous solution was formed by adding 30 g of THF to the residue, a crystal was precipitated with 100 g of methanol. The precipitated crystal was separated by filtration, washed twice with 100 g of methanol, and collected. The collected crystal was vacuum dried at 70° C. Thus, 6.18 g of (A1) was obtained. When the weight average molecular weight (Mw) and dispersity (Mw/Mn) were measured by GPC, the following results were obtained.
(A1): Mw=950, Mw/Mn=1.01

[Synthesis Example 2] Synthesis of Compound (A2)

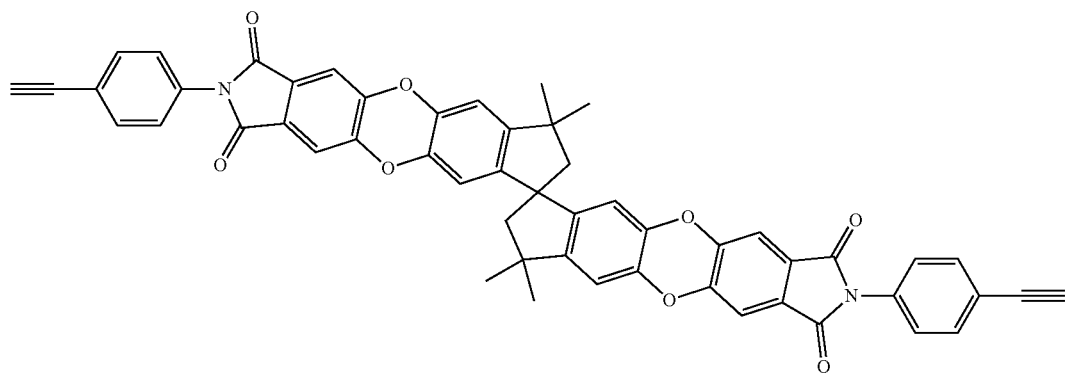

(A2)

A homogeneous solution was formed by adding 30 g of N-methylpyrrolidone to 5.0 g of tetracarboxylic anhydride (B1) under a nitrogen atmosphere at an inner temperature of 40° C. Then, 1.96 g of amine compound (C3) was added and the reaction was allowed to proceed at an inner temperature of 40° C. for 3 hours to obtain an amic acid solution. 1.26 g of pyridine was added to the obtained amic acid solution, and 3.25 g of acetic anhydride was further added dropwise slowly. Then, the reaction was allowed to proceed at an inner temperature of 60° C. for 4 hours for imidization. 100 ml of methyl isobutyl ketone and 50 ml of pure water were added to the reaction liquid for homogenization, then the separated aqueous layer was removed. Further, the organic layer was washed six times with 50 g of a 3% nitric acid aqueous solution and 50 ml of pure water. Then, the organic layer was evaporated under reduced pressure to dryness. After a homogeneous solution was formed by adding 30 g of THF to the residue, a crystal was precipitated with 100 g of methanol. The precipitated crystal was separated by filtration, washed twice with 100 ml of methanol, and collected. The collected crystal was vacuum dried at 70° C. Thus, 6.11 g of (A2) was obtained. When the weight average molecular weight (Mw) and dispersity (Mw/Mn) were measured by GPC, the following results were obtained.
(A2): Mw=900, Mw/Mn=1.00

[Synthesis Example 3] Synthesis of Compound (A3)

A homogeneous solution was formed by adding 30 g of N-methylpyrrolidone to 5.0 g of tetracarboxylic anhydride (B1) under a nitrogen atmosphere at an inner temperature of 40° C. Then, 1.96 g of amine compound (C4) was added and the reaction was allowed to proceed at an inner temperature of 40° C. for 3 hours to obtain an amic acid solution. 1.26 g of pyridine was added to the obtained amic acid solution, and 3.25 g of acetic anhydride was further added dropwise slowly. Then, the reaction was allowed to proceed at an inner temperature of 60° C. for 4 hours for imidization. 100 g of methyl isobutyl ketone and 50 ml of pure water were added to the reaction liquid for homogenization, then the separated aqueous layer was removed. Further, the organic layer was washed six times with 50 g of a 3% nitric acid aqueous solution and 50 ml of pure water. Then, the organic layer was evaporated under reduced pressure to dryness. After a homogeneous solution was formed by adding 30 g of THF to the residue, a crystal was precipitated with 100 g of methanol. The precipitated crystal was separated by filtration, washed twice with 100 ml of methanol, and collected. The collected crystal was vacuum dried at 70° C. Thus, 5.98 g of (A3) was obtained. When the weight average molecular weight (Mw) and dispersity (Mw/Mn) were measured by GPC, the following results were obtained.
(A3): Mw=880, Mw/Mn=1.00

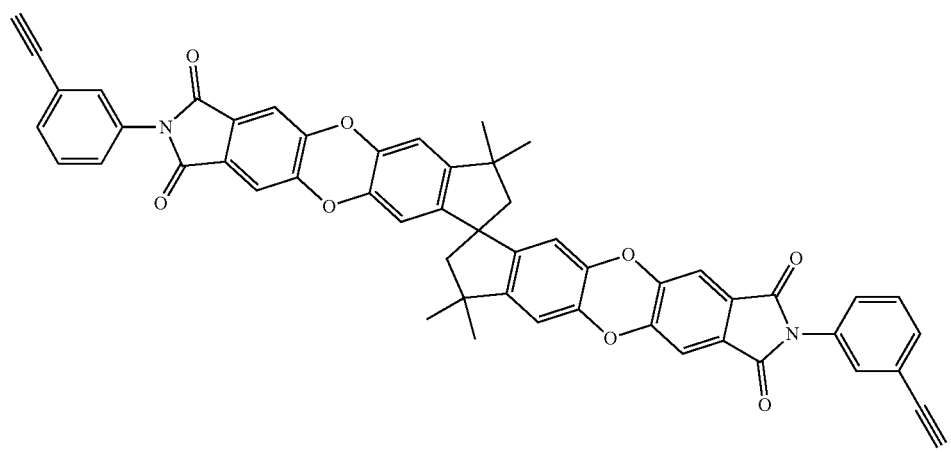

(A3)

[Synthesis Example 4] Synthesis of Compound (A4)

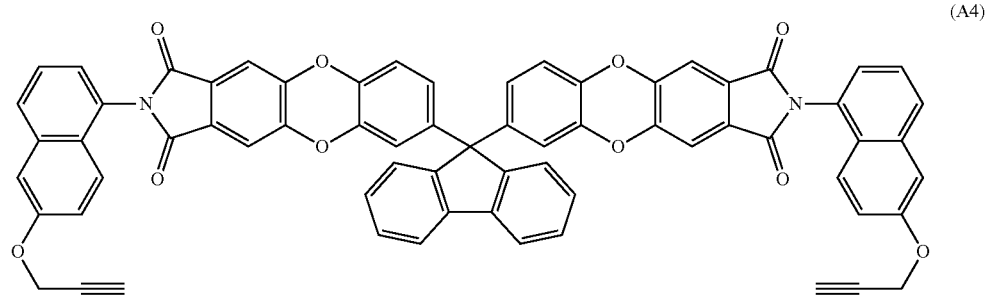 [SMILES: C#CCOc1ccc2c(-n3c(=O)c4cc5oc6ccc(C7(c8ccc9oc%10cc%11c(=O)n(-c%12cccc%13cc(OCC#C)ccc%12%13)c(=O)c%11cc%10oc9c8)c8ccccc8-c8ccccc87)cc6oc5cc4c3=O)cccc2c1]

A homogeneous solution was formed by adding 30 g of N-methylpyrrolidone to 5.0 g of tetracarboxylic anhydride (B2) under a nitrogen atmosphere at an inner temperature of 40° C. Then, 3.09 g of amine compound (C2) was added and the reaction was allowed to proceed at an inner temperature of 40° C. for 3 hours to obtain an amic acid solution. 1.26 g of pyridine was added to the obtained amic acid solution, and 3.25 g of acetic anhydride was further added dropwise slowly. Then, the reaction was allowed to proceed at an inner temperature of 60° C. for 4 hours for imidization. 100 ml of methyl isobutyl ketone and 50 ml of pure water were added to the reaction liquid for homogenization, then the separated aqueous layer was removed. Further, the organic layer was washed six times with 50 g of a 3% nitric acid aqueous solution and 50 ml of pure water. Then, the organic layer was evaporated under reduced pressure to dryness. After a homogeneous solution was formed by adding 30 g of THF to the residue, a crystal was precipitated with 100 g of methanol. The precipitated crystal was separated by filtration, washed twice with 100 ml of methanol, and collected. The collected crystal was vacuum dried at 70° C. Thus, 6.75 g of (A4) was obtained. When the weight average molecular weight (Mw) and dispersity (Mw/Mn) were measured by GPC, the following results were obtained.
(A4): Mw=1120, Mw/Mn=1.03

[Synthesis Example 5] Synthesis of Compound (A5)

A homogeneous solution was formed by adding 30 g of N-methylpyrrolidone to 5.0 g of tetracarboxylic anhydride (B2) under a nitrogen atmosphere at an inner temperature of 40° C. Then, 1.83 g of amine compound (C3) was added and the reaction was allowed to proceed at an inner temperature of 40° C. for 3 hours to obtain an amic acid solution. 1.26 g of pyridine was added to the obtained amic acid solution, and 3.25 g of acetic anhydride was further added dropwise slowly. Then, the reaction was allowed to proceed at an inner temperature of 60° C. for 4 hours for imidization. 100 ml of methyl isobutyl ketone and 50 ml of pure water were added to the reaction liquid for homogenization, then the separated aqueous layer was removed. Further, the organic layer was washed six times with 50 g of a 3% nitric acid aqueous solution and 50 ml of pure water. Then, the organic layer was evaporated under reduced pressure to dryness. After a homogeneous solution was formed by adding 30 g of THF to the residue, a crystal was precipitated with 100 g of methanol. The precipitated crystal was separated by filtration, washed twice with 100 ml of methanol, and collected. The collected crystal was vacuum dried at 70° C. Thus, 6.15 g of (A5) was obtained. When the weight average molecular weight (Mw) and dispersity (Mw/Mn) were measured by GPC, the following results were obtained.
(A5): Mw=840, Mw/Mn=1.01

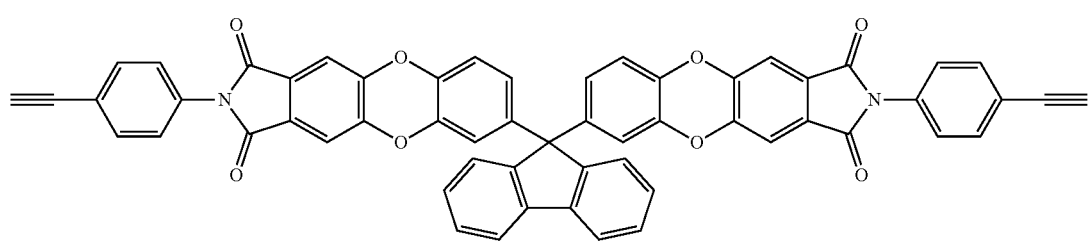

[Synthesis Example 6] Synthesis of Compound (A6)

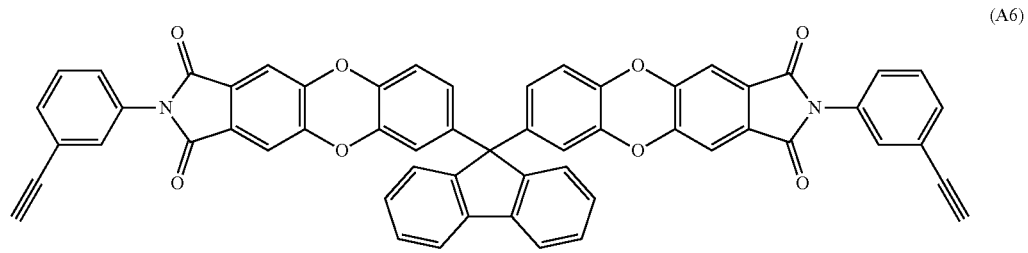 [SMILES: C#Cc1cccc(-n2c(=O)c3cc4oc5ccc(C6(c7ccc8oc9cc%10c(=O)n(-c%11cccc(C#C)c%11)c(=O)c%10cc9oc8c7)c7ccccc7-c7ccccc76)cc5oc4cc3c2=O)c1]

(A6)

A homogeneous solution was formed by adding 30 g of N-methylpyrrolidone to 5.0 g of tetracarboxylic anhydride (B2) under a nitrogen atmosphere at an inner temperature of 40° C. Then, 1.83 g of amine compound (C4) was added and the reaction was allowed to proceed at an inner temperature of 40° C. for 3 hours to obtain an amic acid solution. 1.26 g of pyridine was added to the obtained amic acid solution, and 3.25 g of acetic anhydride was further added dropwise slowly. Then, the reaction was allowed to proceed at an inner temperature of 60° C. for 4 hours for imidization. 100 ml of methyl isobutyl ketone and 50 ml of pure water were added to the reaction liquid for homogenization, then the separated aqueous layer was removed. Further, the organic layer was washed six times with 50 g of a 3% nitric acid aqueous solution and 50 ml of pure water. Then, the organic layer was evaporated under reduced pressure to dryness. After a homogeneous solution was formed by adding 30 g of THF to the residue, a crystal was precipitated with 100 g of methanol. The precipitated crystal was separated by filtration, washed twice with 100 ml of methanol, and collected. The collected crystal was vacuum dried at 70° C. Thus, 6.09 g of (A6) was obtained. When the weight average molecular weight (Mw) and dispersity (Mw/Mn) were measured by GPC, the following results were obtained.
(A6): Mw=820, Mw/Mn=1.00

[Comparative Synthesis Example 1] Synthesis of Compound (R1)

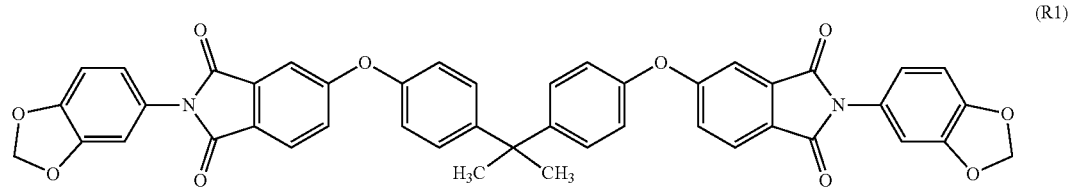 [SMILES: CC(C)(c1ccc(Oc2ccc3c(c2)C(=O)N(c2ccc4c(c2)OCO4)C3=O)cc1)c1ccc(Oc2ccc3c(c2)C(=O)N(c2ccc4c(c2)OCO4)C3=O)cc1]

(R1)

A homogeneous solution was formed by adding 30 g of N-methylpyrrolidone to 5.00 g of tetracarboxylic anhydride (B3) under a nitrogen atmosphere at an inner temperature of 40° C. Then, 2.77 g of amine compound (C5) was added and the reaction was allowed to proceed at an inner temperature of 40° C. for 3 hours to obtain an amic acid solution. 100 g of o-xylene was added to the obtained amic acid solution, and while removing the generated low-boiling substance and the generated water from the system, the reaction was allowed to proceed at an inner temperature of 150° C. for 9 hours for dehydrating imidization. After completion of the reaction, the solution was cooled to room temperature and a crystal was precipitated in 300 g of methanol. The precipitated crystal was separated by filtration, washed twice with 100 ml of methanol, and collected. The collected crystal was vacuum dried at 70° C. Thus, 6.34 g of (R1) was obtained. When the weight average molecular weight (Mw) and dispersity (Mw/Mn) were measured by GPC, the following results were obtained.
(R1): Mw=830, Mw/Mn=1.01

[Comparative Synthesis Example 2] Synthesis of Compound (R2)

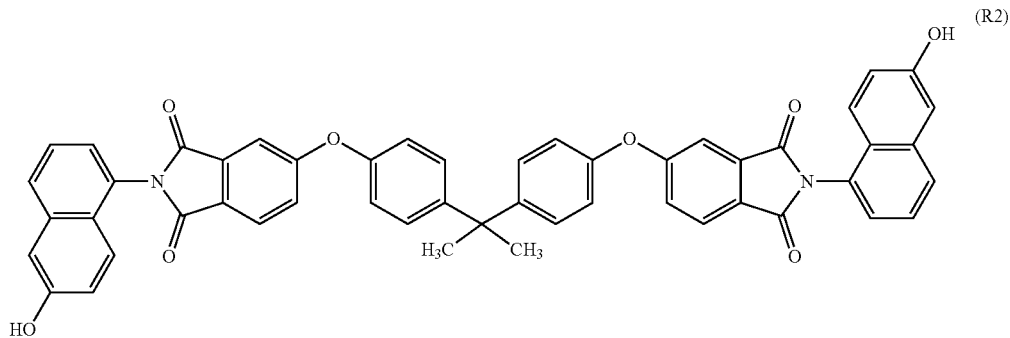 [SMILES: CC(C)(c1ccc(Oc2ccc3c(c2)C(=O)N(c2cccc4cc(O)ccc24)C3=O)cc1)c1ccc(Oc2ccc3c(c2)C(=O)N(c2cccc4cc(O)ccc24)C3=O)cc1]

A homogeneous solution was formed by adding 30 g of N-methylpyrrolidone to 5.00 g of tetracarboxylic anhydride (B3) under a nitrogen atmosphere at an inner temperature of 40° C. Then, 3.21 g of amine compound (C6) was added and the reaction was allowed to proceed at an inner temperature of 40° C. for 3 hours to obtain an amic acid solution. 100 g of o-xylene was added to the obtained amic acid solution, and while removing the generated low-boiling substance and the generated water from the system, the reaction was allowed to proceed at an inner temperature of 150° C. for 9 hours for dehydrating imidization. After completion of the reaction, the solution was cooled to room temperature and a crystal was precipitated in 300 g of methanol. The precipitated crystal was separated by filtration, washed twice with 100 ml of methanol, and collected. The collected crystal was vacuum dried at 70° C. Thus, (R2) was obtained. When the weight average molecular weight (Mw) and dispersity (Mw/Mn) were measured by GPC, the following results were obtained.
(R2): Mw=890, Mw/Mn=1.03

[Comparative Synthesis Example 3] Synthesis of Compound (R3) for Comparative Example A homogeneous solution was formed by adding 30 g of N-methylpyrrolidone to 5.0 g of tetracarboxylic anhydride (B3) under a nitrogen atmosphere at an inner temperature of 40° C. Then, 3.21 g of amine compound (C4) was added and the reaction was allowed to proceed at an inner temperature of 40° C. for 3 hours to obtain an amic acid solution. 1.26 g of pyridine was added to the obtained amic acid solution, and 3.25 g of acetic anhydride was further added dropwise slowly. Then, the reaction was allowed to proceed at an inner temperature of 60° C. for 4 hours for imidization. 100 ml of methyl isobutyl ketone and 50 ml of pure water were added to the reaction liquid for homogenization, then the separated aqueous layer was removed. Further, the organic layer was washed six times with 50 g of a 3% nitric acid aqueous solution and 50 ml of pure water. Then, the organic layer was evaporated under reduced pressure to dryness. After a homogeneous solution was formed by adding 30 g of THF to the residue, a crystal was precipitated with 100 g of methanol. The precipitated crystal was separated by filtration, washed twice with 100 ml of methanol, and collected. The collected crystal was vacuum dried at 70° C. Thus, 6.09 g of (R3) was obtained. When the weight average molecular weight (Mw) and dispersity (Mw/Mn) were measured by GPC, the following results were obtained.
(R3): Mw=850, Mw/Mn=1.01

The structural formula, weight average molecular weight (Mw), and dispersity (Mw/Mn) of the compounds in Synthesis Examples 1 to 6 obtained above are listed in Tables 1 and 2. Additionally, Mw and Mw/Mn of the compounds (R1) to (R3) used in Comparative Examples are also shown in Table 3.

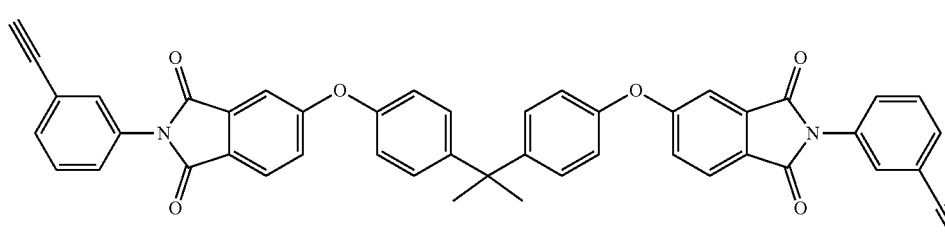

TABLE 1

| Synthesis Example | Compound | Mw | Mw/Mn |
|---|---|---|---|
| 1 | (A1) | 950 | 1.01 |
| 2 | (A2) | 900 | 1.00 |
| 3 | (A3) | 880 | 1.00 |

TABLE 2

| Synthesis Example | Compound | Mw | Mw/Mn |
|---|---|---|---|
| 4 | (A4) | 1120 | 1.03 |
| 5 | (A5) | 840 | 1.01 |

TABLE 2-continued

| Synthesis Example | Compound | | Mw | Mw/Mn |
|---|---|---|---|---|
| 6 | [chemical structure] | (A6) | 820 | 1.00 |

TABLE 3

| Synthesis Example | Compound | | Mw | Mw/Mn |
|---|---|---|---|---|
| 7 | [chemical structure] | (R1) | 830 | 1.01 |
| 8 | [chemical structure] | (R2) | 890 | 1.03 |
| 9 | [chemical structure] | (R3) | 850 | 1.01 |

Preparation of Materials (UDL-1 to -9, Comparative UDL-1 to -3) for Forming Organic Film Each of the compounds (A1) to (A6) and (R1) to (R3), and as a high-boiling-point solvent, (S1) 1,6-diacetoxyhexane having a boiling point of 260° C., (S2) γ-butyrolactone having a boiling point of 204° C., and (S3) tripropylene glycol monomethyl ether having a boiling point of 242° C. were dissolved in a solvent containing propylene glycol monomethyl ether acetate (PGMEA) or cyclohexanone (CyHO) and 0.1 mass % of FC-4430 (manufactured by Sumitomo 3M Ltd.) in proportions shown in Table 4. The solution was filtered through a 0.1-μm filter made of a fluorinated resin to prepare materials (UDL-1 to -9, Comparative Examples UDL-1 to -3) for forming an organic film.

TABLE 4

| Material for forming organic film | Compound (parts by mass) | High-boiling-point solvent (parts by mass) | CYHO (parts by mass) | PGMEA (parts by mass) |
|---|---|---|---|---|
| UDL-1 | A1(10) | — | — | 90 |
| UDL-2 | A2(10) | — | — | 90 |
| UDL-3 | A3(10) | — | — | 90 |

TABLE 4-continued

| Material for forming organic film | Compound (parts by mass) | High-boiling-point solvent (parts by mass) | CYHO (parts by mass) | PGMEA (parts by mass) |
|---|---|---|---|---|
| UDL-4 | A4(10) | — | — | 90 |
| UDL-5 | A5(10) | — | — | 90 |
| UDL-6 | A6(10) | — | — | 90 |
| UDL-7 | A2(10) | S1(10) | — | 80 |
| UDL-8 | A4(10) | S2(10) | — | 80 |
| UDL-9 | A6(10) | S3(10) | — | 80 |
| Comparative UDL-1 | R1(10) | — | 90 | — |
| Comparative UDL-2 | R2(10) | — | 90 | — |
| Comparative UDL-3 | R3(10) | — | 90 | — |

Example 1: Solvent Resistance Measurement (Examples 1-1 to 1-9, Comparative Examples 1-1 to 1-3)

A silicon substrate was coated with the materials (UDL-1 to -9, comparative UDL-1 to -3) for forming an organic film prepared above and baked at 450° C. for 60 seconds under such a nitrogen stream that the oxygen concentration was controlled to 0.2% or less. Then, the film thickness was measured. A PGMEA solvent was dispensed on the film and allowed to stand for 30 seconds. The resultant was spin-dried and baked at 100° C. for 60 seconds to evaporate the PGMEA, and the film thickness was measured. A difference in film thicknesses before and after the PGMEA treatment was determined.

TABLE 5

| | Material for forming organic film | Film thickness after film formation: a (Å) | Film thickness after PGMEA treatment: b (Å) | b/a × 100 (%) |
|---|---|---|---|---|
| Example 1-1 | UDL-1 | 2001 | 1996 | 99.8 |
| Example 1-2 | UDL-2 | 2002 | 2001 | 100.0 |
| Example 1-3 | UDL-3 | 2009 | 2008 | 100.0 |
| Example 1-4 | UDL-4 | 2006 | 2003 | 99.9 |
| Example 1-5 | UDL-5 | 2008 | 2007 | 100.0 |
| Example 1-6 | UDL-6 | 2001 | 2000 | 100.0 |
| Example 1-7 | UDL-7 | 2000 | 1999 | 100.0 |
| Example 1-8 | UDL-8 | 1999 | 1996 | 99.8 |
| Example 1-9 | UDL-9 | 1994 | 1994 | 100.0 |
| Comparative Example 1-1 | Comparative UDL-1 | 1995 | 657 | 33.0 |
| Comparative Example 1-2 | Comparative UDL-2 | 2000 | 680 | 33.9 |
| Comparative Example 1-3 | Comparative UDL-3 | 1999 | 1996 | 99.8 |

As shown in Table 5, in the inventive materials for forming an organic film (Examples 1-1 to 1-9), the film remaining percentages after the PGMEA treatment were 99.8% or more. This indicates that the crosslinking reaction took place even under the nitrogen atmosphere, and sufficient solvent resistance was exhibited. In contrast, in Comparative Examples 1-1 and 1-2, the film remaining percentages after the PGMEA treatment were less than 50% since there were no substituents to be linking groups. Therefore, a curing reaction did not take place, and solvent resistance was not exhibited. In Comparative Example 1-3, in which an ethynyl group was contained, solvent resistance was exhibited, and film remaining percentage was not less than 99.8%. These results indicate that the substituent represented by $R_1$, introduced as a substituent is functioning effectively as a thermal linking group.

Example 2: Heat Resistance Evaluation (Examples 2-1 to 2-9, Comparative Examples 2-1 to 2-3)

The materials (UDL-1 to -9, comparative UDL-1 to -3) for forming an organic film were each applied onto a silicon substrate and baked in the atmosphere at 180° C. to form a coating film of 200 nm. The film thickness was measured. This substrate was further baked at 450° C. for 10 minutes under such a nitrogen stream that the oxygen concentration was controlled to 0.2% or less. Then, the film thickness was measured. The results are shown in Table 6.

TABLE 6

| | Material for forming organic film | Film thickness at 180° C.: A(Å) | Film thickness at 450° C.: B(Å) | Film remaining percentage % (B/A) |
|---|---|---|---|---|
| Example 2-1 | UDL-1 | 2020 | 1962 | 97.1 |
| Example 2-2 | UDL-2 | 2010 | 1994 | 99.2 |
| Example 2-3 | UDL-3 | 1999 | 1981 | 99.1 |
| Example 2-4 | UDL-4 | 1983 | 1941 | 97.9 |
| Example 2-5 | UDL-5 | 1993 | 1979 | 99.3 |
| Example 2-6 | UDL-6 | 2008 | 1993 | 99.2 |
| Example 2-7 | UDL-7 | 1998 | 1980 | 99.1 |
| Example 2-8 | UDL-8 | 2008 | 1963 | 97.8 |
| Example 2-9 | UDL-9 | 2004 | 1992 | 99.4 |
| Comparative Example 2-1 | Comparative UDL-1 | 1984 | 764 | 38.5 |
| Comparative Example 2-2 | Comparative UDL-2 | 2001 | 798 | 39.9 |
| Comparative Example 2-3 | Comparative UDL-3 | 1979 | 1949 | 98.5 |

As shown in Table 6, in the inventive materials for forming an organic film (Examples 2-1 to 2-9), the film thicknesses were decreased by less than 3% even after the baking at 450° C. for 10 minutes. The inventive material for forming an organic film makes it possible to form an organic film having high heat resistance even under high-temperature conditions of 450° C. In particular, in Examples 2-2, 2-3, 2-5, 2-6, 2-7, and 2-9, in which $R_1$ has an ethynyl group, the decrease in the film thicknesses was suppressed to less than 1% even after the baking at 450° C. for 10 minutes. Thus, it can be observed that heat resistance was particularly excellent. In contrast, in Comparative Examples 2-1 and 2-2, in which there was no crosslinking structure, large film thickness decrease exceeding 60% occurred. Thus, it can be observed that the film has low heat resistance because there is no terminal structure that contributes to a crosslinking reaction.

Example 3: Filling Property Evaluation (Examples 3-1 to 3-9, Comparative Examples 3-1 to 3-3)

As shown in FIG. 3, the materials (UDL-1 to -9, comparative UDL-1 to -3) for forming an organic film were each applied onto a SiO$_2$ wafer substrate having a dense hole pattern (hole diameter: 0.16 µm, hole depth: 0.50 µm, distance between the centers of two adjacent holes: 0.32 µm) and baked with a hot plate at 450° C. for 60 seconds under such a nitrogen stream that the oxygen concentration was controlled to 0.2% or less. Thereby, an organic film 8 was formed. The substrate used was a base substrate 7 (SiO$_2$ wafer substrate) having a dense hole pattern as shown in FIG. 3 (G) (top view) and (H) (sectional view). The sectional shapes of the resulting wafer substrates were observed with a scanning electron microscope (SEM) to check whether or not the holes were filled with the organic film without voids (space). Table 7 shows the results. If an organic film material having poor filling property is used, voids occur inside the holes in this evaluation. When an organic film material having good filling property is used, the holes are filled with the organic film 8 without voids in this evaluation as shown in FIG. 3 (I).

TABLE 7

| | Material for forming organic film | Presence/ absence of voids |
|---|---|---|
| Example 3-1 | UDL-1 | Absent |
| Example 3-2 | UDL-2 | Absent |
| Example 3-3 | UDL-3 | Absent |
| Example 3-4 | UDL-4 | Absent |
| Example 3-5 | UDL-5 | Absent |
| Example 3-6 | UDL-6 | Absent |
| Example 3-7 | UDL-7 | Absent |
| Example 3-8 | UDL-8 | Absent |
| Example 3-9 | UDL-9 | Absent |
| Comparative Example 3-1 | Comparative UDL-1 | Present |
| Comparative Example 3-2 | Comparative UDL-2 | Present |
| Comparative Example 3-3 | Comparative UDL-3 | Absent |

As shown in Table 7, it was confirmed that the inventive materials for forming an organic film (Examples 3-1 to 3-9) enabled the hole patterns to be filled without voids being generated, and that the filling property was favorable. Meanwhile, in Comparative Examples 3-1 and 3-2, voids caused by insufficient heat resistance had occurred, in accordance with the results of Example 2. From these results, it was confirmed that the inventive material for forming an organic film had a favorable filling property.

Example 4: Planarizing Property Evaluation (Examples 4-1 to 4-9, Comparative Examples 4-1 to 4-3)

The materials (UDL-1 to -9, comparative UDL-1 to -3) for forming an organic film were each applied onto a base substrate 9 (SiO$_2$ wafer substrate) having a giant isolated trench pattern (FIG. 4 (J), trench width: 10 μm, trench depth: 0.10 μm), and baked at 450° C. for 60 seconds under such a nitrogen stream that the oxygen concentration was controlled to 0.2% or less. Then, a step (delta 10 in FIG. 4 (K)) between the trench portion and the non-trench portion of an organic film 10 was observed with an atomic force microscope (AFM) NX10 manufactured by Park systems Corp. Table 8 shows the results. In this evaluation, the smaller the step, the better the planarizing property. Note that, in this evaluation, a trench pattern having a depth of 0.10 μm was planarized using an organic film material generally having a film thickness of approximately 0.2 μm. This is a severe evaluation condition to evaluate the planarizing property.

TABLE 8

| | Material for forming organic film | Step (nm) |
|---|---|---|
| Example 4-1 | UDL-1 | 30 |
| Example 4-2 | UDL-2 | 20 |
| Example 4-3 | UDL-3 | 15 |
| Example 4-4 | UDL-4 | 30 |
| Example 4-5 | UDL-5 | 20 |
| Example 4-6 | UDL-6 | 15 |
| Example 4-7 | UDL-7 | 15 |
| Example 4-8 | UDL-8 | 25 |
| Example 4-9 | UDL-9 | 10 |
| Comparative Example 4-1 | Comparative UDL-1 | 85 |
| Comparative Example 4-2 | Comparative UDL-2 | 90 |
| Comparative Example 4-3 | Comparative UDL-3 | 35 |

As shown in Table 8, it was confirmed that in the inventive materials for forming an organic film (Examples 4-1 to 4-9), the organic film had smaller steps between the trench portion and the non-trench portion than those in Comparative Examples 4-1 to 4-3, and the planarizing property was excellent. In Comparative Examples 4-1 and 4-2, heat resistance was insufficient, as shown by the results of the heat resistance evaluation, and the films shrank considerably during the baking at 450° C., resulting in degraded flatness. Meanwhile, in Comparative Example 4-3, there were ethynyl groups as crosslinking groups, so that heat resistance was excellent. However, since there was no structure of an imide compound as in the present invention, flowability was not improved, resulting in poor flatness. Furthermore, comparing Examples 4-7 to 4-9 in which the high-boiling-point solvent was added with Examples 4-2, 4-4, and 4-6 in which the high-boiling-point solvent was not added respectively, it is revealed that adding the high-boiling-point solvent further improves planarizing property. From these results, it is revealed that the inventive material for forming an organic film suppresses film shrinking during high-temperature baking, since the material is excellent in heat resistance, and exhibits an excellent planarizing property.

Example 5: Patterning Test (Examples 5-1 to 5-9, Comparative Example 5-1)

The materials (UDL-1 to -9, comparative UDL-3) for forming an organic film were each applied onto a silicon wafer substrate on which a SiO$_2$ film of 300 nm had been formed. Then, the resulting substrate was baked at 450° C. for 60 seconds under such a nitrogen stream that the oxygen concentration was controlled to 0.2% or less. Thereby, an organic film (resist underlayer film) was formed. A CVD-SiON hard mask was formed thereon, and further, an organic antireflective coating material (ARC-29A: manufactured by Nissan Chemical Industries, Ltd.) was applied and baked at 210° C. for 60 seconds to form an organic antireflective coating having a film thickness of 80 nm. A monolayer resist for ArF was applied thereon as a resist upper layer film material and baked at 105° C. for 60 seconds to form a photoresist film having a film thickness of 100 nm. A liquid immersion top coat material (TC-1) was applied on the photoresist film and baked at 90° C. for 60 seconds to form a top coat having a film thickness of 50 nm. Note that in Comparative Examples UDL-1 and UDL-2, it was not possible to form a CVD-SiON hard mask due to poor heat resistance, and therefore, it was not possible to proceed to the subsequent patterning test.

The resist upper layer film material (monolayer resist for ArF) was prepared by: dissolving a polymer (RP1), an acid generator (PAG1), and a basic compound (Amine1) into a solvent containing 0.1 mass % FC-430 (manufactured by Sumitomo 3M Ltd.) in proportions shown in Table 9; and filtering the solution through a 0.1-μm filter made of a fluorinated resin.

TABLE 9

| | Polymer (parts by mass) | Acid generator (parts by mass) | Basic compound (parts by mass) | Solvent (parts by mass) |
|---|---|---|---|---|
| Monolayer resist for ArF | RP1 (100) | PAG1 (6.6) | Amine1 (0.8) | PGMEA (2500) |

The polymer (RP1), acid generator (PAG1), and basic compound (Amine1) used are shown below.

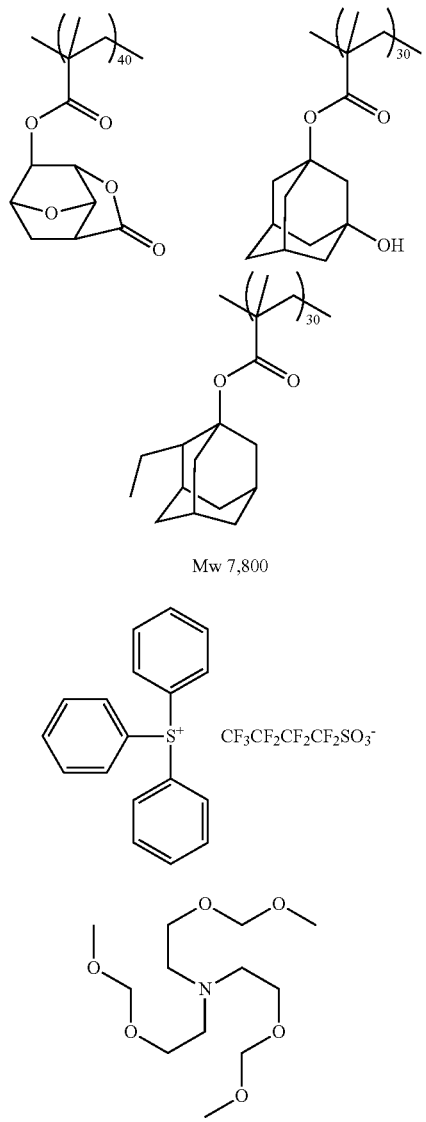

Mw 7,800

PAG1

Amine1

The liquid immersion top coat material (TC-1) was prepared by: dissolving a top coat polymer (PP1) into organic solvents in proportions shown in Table 10; and filtering the solution through a 0.1-μm filter made of a fluorinated resin.

TABLE 10

| | Polymer (parts by mass) | Organic solvent (parts by mass) |
|---|---|---|
| TC-1 | PP1 (100) | Diisoamyl ether (2700) 2-methyl-1-butanol (270) |

The polymer (PP1) used is shown below.

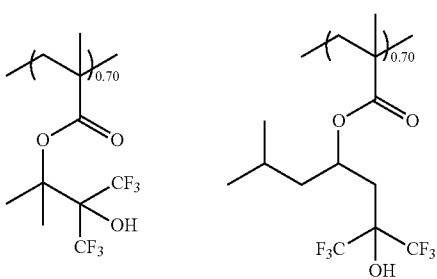

Mw 8,800
Mw/Mn 1.69

Next, the resulting substrate was exposed to light with an ArF liquid immersion exposure apparatus (NSR-S610C manufactured by Nikon Corporation, NA: 1.30, σ: 0.98/0.65, 350 s-polarized dipole illumination, 6% halftone phase shift mask), baked at 100° C. for 60 seconds (PEB), and developed with a 2.38 mass % tetramethylammonium hydroxide (TMAH) aqueous solution for 30 seconds. Thus, a 55 nm 1:1 positive line and space pattern was obtained.

Next, the organic antireflective coating and the CVD-SiON hard mask were processed by dry etching while using the resist pattern as a mask with an etching apparatus Telius manufactured by Tokyo Electron Limited to form a hard mask pattern. The organic film was etched while using the obtained hard mask pattern as a mask to form an organic film pattern. The $SiO_2$ film was processed by etching while using the obtained organic film pattern as a mask. The etching conditions were as described below.

Conditions for transferring the resist pattern to the SiON hard mask.
Chamber pressure: 10.0 Pa
RF power: 1,500 W
$CF_4$ gas flow rate: 75 sccm
$O_2$ gas flow rate: 15 sccm
Time: 15 sec Conditions for transferring the hard mask pattern to the organic film.
Chamber pressure: 2.0 Pa
RF power: 500 W
Ar gas flow rate: 75 sccm
$O_2$ gas flow rate: 45 sccm
Time: 120 sec Conditions for transferring the organic film pattern to the $SiO_2$ film.
Chamber pressure: 2.0 Pa
RF power: 2,200 W
$C_5F_{12}$ gas flow rate: 20 sccm
$C_2F_6$ gas flow rate: 10 sccm
Ar gas flow rate: 300 sccm
$O_2$ gas flow rate: 60 sccm
Time: 90 sec The pattern cross sections were observed with an electron microscope (S-4700) manufactured by Hitachi, Ltd. Table 11 shows the results.

TABLE 11

|  | Material for forming organic film | Pattern profile after etching for transferring to substrate |
|---|---|---|
| Example 5-1 | UDL-1 | Vertical profile |
| Example 5-2 | UDL-2 | Vertical profile |
| Example 5-3 | UDL-3 | Vertical profile |
| Example 5-4 | UDL-4 | Vertical profile |
| Example 5-5 | UDL-5 | Vertical profile |
| Example 5-6 | UDL-6 | Vertical profile |
| Example 5-7 | UDL-7 | Vertical profile |
| Example 5-8 | UDL-8 | Vertical profile |
| Example 5-9 | UDL-9 | Vertical profile |
| Comparative Example 5-1 | Comparative UDL-3 | Pattern collapse |

As shown in Table 11, as a result of any of the inventive materials for forming an organic film (Examples 5-1 to 5-9), the resist upper layer film pattern was favorably transferred to the final substrate, confirming that the inventive materials for forming an organic film are suitably used in fine processing according to the multilayer resist method. In Comparative Example 5-1, it was possible to form a CVD-SiON hard mask on the underlayer film (organic film), but the film peeled off from the substrate when forming a pattern due to insufficient adhesiveness of the film. Therefore, it was not possible to form a pattern.

Example 6: Adhesiveness Test (Examples 6-1 to 6-9, Comparative Example 6-1

The materials (UDL-1 to -9, comparative UDL-3) for forming an organic film were each applied onto a SiO$_2$ wafer substrate and baked at 450° C. for 60 seconds under such a nitrogen stream that the oxygen concentration was controlled to 0.2% or less. Thus, an organic film with a film thickness of 200 nm was formed. This wafer with an organic film was cut into a 1×1 cm square, and an aluminum pin with epoxy adhesive was fastened to the cut wafer with a dedicated jig. Thereafter, the assembly was heated with an oven at 150° C. for 1 hour to bond the aluminum pin to the substrate. After cooling to room temperature, initial adhesiveness was evaluated based on the resistance force by a thin-film adhesion strength measurement apparatus (Sebastian Five-A).

FIG. 5 shows an explanatory diagram showing an adhesiveness measurement method. In FIG. 5, reference number 11 denotes a silicon wafer (substrate), 12 denotes a cured film, 13 denotes an aluminum pin with adhesive, 14 denotes a support, 15 denotes a grip, and 16 denotes a tensile direction. The adhesion is an average of 12 measurement points, and a larger value indicates that the organic film has higher adhesiveness with respect to the substrate. The adhesiveness was evaluated by comparing the obtained values. Table 12 shows the results.

TABLE 12

|  | Material for forming organic film | Adhesion (mN) |
|---|---|---|
| Example 6-1 | UDL-1 | 590 |
| Example 6-2 | UDL-2 | 540 |
| Example 6-3 | UDL-3 | 560 |
| Example 6-4 | UDL-4 | 590 |
| Example 6-5 | UDL-5 | 540 |
| Example 6-6 | UDL-6 | 560 |
| Example 6-7 | UDL-7 | 540 |
| Example 6-8 | UDL-8 | 580 |
| Example 6-9 | UDL-9 | 550 |
| Comparative Example 6-1 | Comparative UDL-3 | 340 |

As shown in Table 12, it can be observed that the organic film materials using polyimide, being the inventive compound for forming an organic film (Examples 6-1 to 6-9), were more excellent in adhesion compared with Comparative Example 6-1, where it was not possible to form a pattern, as in the patterning test result of Example 5. It was also confirmed from the results of the adhesiveness test that the inventive materials for forming an organic film can be used favorably as patterning materials.

From the above, it was revealed that the inventive materials for forming an organic film containing the inventive compound for forming an organic film have heat resistance to 400° C. or higher, and high filling and planarizing properties even in an oxygen-free inert gas. Thus, the inventive materials for forming an organic film are quite useful as organic film materials used in multilayer resist methods. Moreover, the inventive patterning processes using these materials can precisely form a fine pattern even when a body to be processed is a stepped substrate.

It should be noted that the present invention is not limited to the above-described embodiments. The embodiments are just examples, and any examples that have substantially the same feature and demonstrate the same functions and effects as those in the technical concept disclosed in claims of the present invention are included in the technical scope of the present invention.

The invention claimed is:
1. A material for forming an organic film, comprising:
(A) a compound for forming an organic film shown by the following general formula (1A); and
(B) an organic solvent,

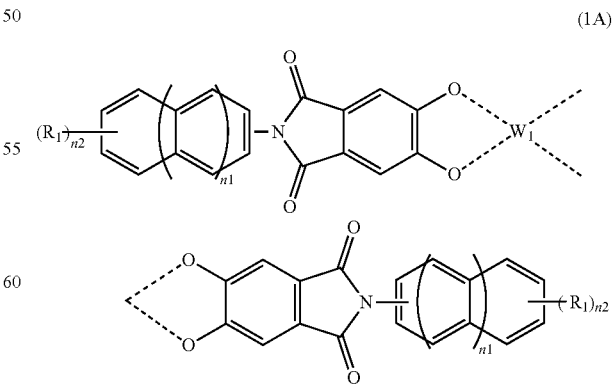

wherein W$_1$ represents a tetravalent organic group, n1 represents an integer of 0 or 1, n2 represents an integer of 1 to 3, and $R_1$ represents any one or more of the following general formulae (1B)

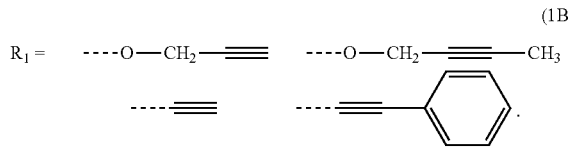

2. The material for forming an organic film according to claim 1, wherein the component (A) is a compound shown by the following general formula (1C) or (1D),

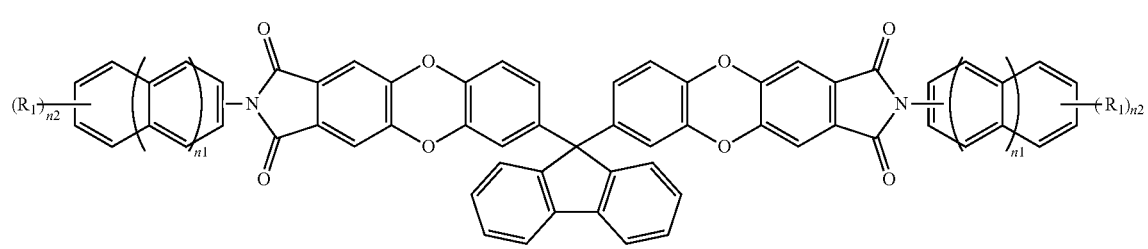

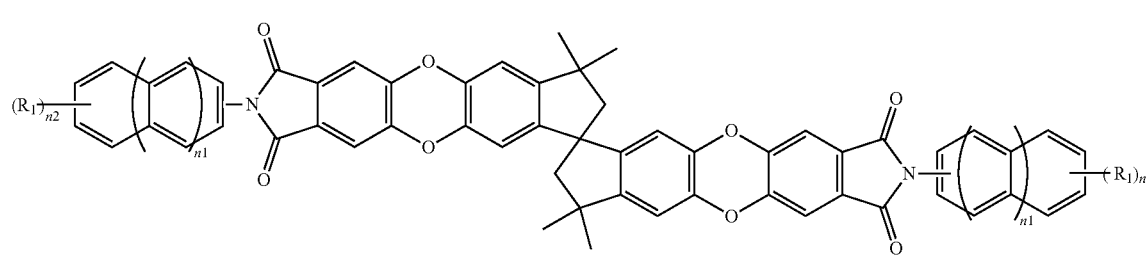

wherein n1, n2, and $R_1$ in the formulae have the same meanings as defined above.

3. The material for forming an organic film according to claim 1, wherein the component (A) is a compound shown by the following general formula (1E) or (1F)

4. The material for forming an organic film according to claim 1, wherein the component (A) satisfies $1.00 \leq Mw/Mn \leq 1.10$ where Mw is a weight average molecular weight and Mn is a number average molecular weight measured by gel permeation chromatography in terms of polystyrene.

5. The material for forming an organic film according to claim 1, wherein the component (B) is a mixture of one or more kinds of organic solvent having a boiling point of lower than 180° C. and one or more kinds of organic solvent having a boiling point of 180° C. or higher.

6. The material for forming an organic film according to claim 1, further comprising at least one of (C) an acid generator, (D) a surfactant, (E) a crosslinking agent, and (F) a plasticizer.

7. A substrate for manufacturing a semiconductor device, comprising an organic film on the substrate, the organic film being a cured film of the material for forming an organic film according to claim 1.

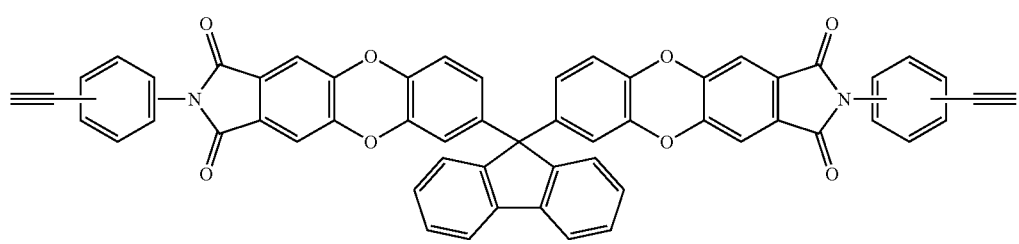

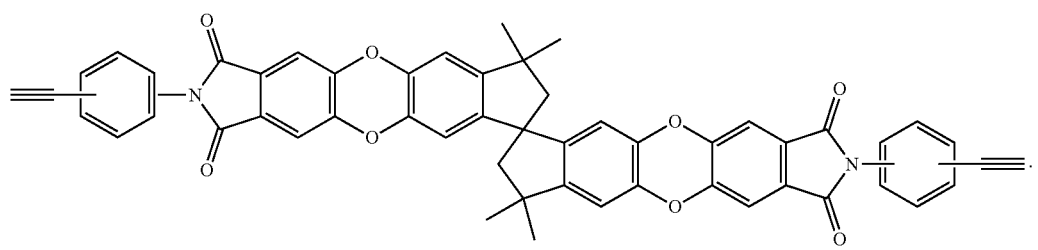

8. A method for forming an organic film employed in a semiconductor device manufacturing process, the method comprising:
- spin-coating a substrate to be processed with the material for forming an organic film according to claim 1;
- heating the substrate to be processed coated with the material for forming an organic film in air at a temperature of 50° C. or higher to 250° C. or lower for 5 seconds to 600 seconds to form a coating film; and
- then performing a heat treatment under an inert gas atmosphere at a temperature of 200° C. or higher to 600° C. or lower for 10 seconds to 7200 seconds to obtain a cured film.

9. A patterning process comprising:
- forming an organic film by using the material for forming an organic film according to claim 1 on a body to be processed;
- forming a silicon-containing resist middle layer film by using a silicon-containing resist middle layer film material on the organic film;
- forming an organic antireflective coating on the silicon-containing resist middle layer film;
- forming a resist upper layer film by using a photoresist composition on the organic antireflective coating, so that a 4-layered film structure is constructed;
- forming a circuit pattern in the resist upper layer film;
- transferring the pattern to the organic antireflective coating and the silicon-containing resist middle layer film by etching while using the resist upper layer film having the formed pattern as a mask;
- transferring the pattern to the organic film by etching while using the silicon-containing resist middle layer film having the transferred pattern as a mask; and
- further transferring the pattern to the body to be processed by etching while using the organic film having the transferred pattern as a mask.

10. A patterning process comprising:
- forming an organic film by using the material for forming an organic film according to claim 1 on a body to be processed;
- forming an inorganic hard mask selected from a silicon oxide film, a silicon nitride film, a silicon oxynitride film, a titanium oxide film, and a titanium nitride film on the organic film;
- forming an organic antireflective coating on the inorganic hard mask;
- forming a resist upper layer film by using a photoresist composition on the organic antireflective coating, so that a 4-layered film structure is constructed;
- forming a circuit pattern in the resist upper layer film;
- transferring the pattern to the organic antireflective coating and the inorganic hard mask by etching while using the resist upper layer film having the formed pattern as a mask;
- transferring the pattern to the organic film by etching while using the inorganic hard mask having the transferred pattern as a mask; and
- further transferring the pattern to the body to be processed by etching while using the organic film having the transferred pattern as a mask.

11. A method for forming an organic film employed in a semiconductor device manufacturing process, the method comprising:
- spin-coating a substrate to be processed with the material for forming an organic film according to claim 1; and
- heating the substrate to be processed coated with the material for forming an organic film under an inert gas atmosphere at a temperature of 50° C. or higher to 600° C. or lower for 10 seconds to 7200 seconds to obtain a cured film.

12. The method for forming an organic film according to claim 11, wherein the inert gas has an oxygen concentration of 1% or less.

13. The method for forming an organic film according to claim 11, wherein the substrate to be processed has a structure or a step with a height of 30 nm or more and 100 nm or less.

14. A patterning process comprising:
- forming an organic film by using the material for forming an organic film according to claim 1 on a body to be processed;
- forming an inorganic hard mask selected from a silicon oxide film, a silicon nitride film, a silicon oxynitride film, a titanium oxide film, and a titanium nitride film on the organic film;
- forming a resist upper layer film by using a photoresist composition on the inorganic hard mask;
- forming a circuit pattern in the resist upper layer film;
- transferring the pattern to the inorganic hard mask by etching while using the resist upper layer film having the formed pattern as a mask;
- transferring the pattern to the organic film by etching while using the inorganic hard mask having the transferred pattern as a mask; and
- further transferring the pattern to the body to be processed by etching while using the organic film having the transferred pattern as a mask.

15. The patterning process according to claim 14, wherein the inorganic hard mask is formed by a CVD method or an ALD method.

16. A patterning process comprising:
- forming an organic film by using the material for forming an organic film according to claim 1 on a body to be processed;
- forming a silicon-containing resist middle layer film by using a silicon-containing resist middle layer film material on the organic film;
- forming a resist upper layer film by using a photoresist composition on the silicon-containing resist middle layer film;
- forming a circuit pattern in the resist upper layer film;
- transferring the pattern to the silicon-containing resist middle layer film by etching while using the resist upper layer film having the formed pattern as a mask;
- transferring the pattern to the organic film by etching while using the silicon-containing resist middle layer film having the transferred pattern as a mask; and
- further transferring the pattern to the body to be processed by etching while using the organic film having the transferred pattern as a mask.

17. The patterning process according to claim 16, wherein the circuit pattern is formed by a lithography using light with a wavelength of 10 nm or more to 300 nm or less, a direct drawing by electron beam, a nanoimprinting, or a combination thereof.

18. The patterning process according to claim 16, wherein when the circuit pattern is formed, the circuit pattern is developed by alkaline development or with an organic solvent.

19. The patterning process according to claim 16, wherein the body to be processed is a semiconductor device substrate or the semiconductor device substrate coated with any of a metal film, a metal carbide film, a metal oxide film, a metal nitride film, a metal oxycarbide film, and a metal oxynitride film.

20. The patterning process according to claim 19, wherein as the body to be processed, a body to be processed comprising silicon, titanium, tungsten, hafnium, zirconium, chromium, germanium, copper, silver, gold, aluminum, indium, gallium, arsenic, palladium, iron, tantalum, iridium, cobalt, manganese, molybdenum, or an alloy thereof is used.

21. A compound for forming an organic film shown by the following general formula (1A),

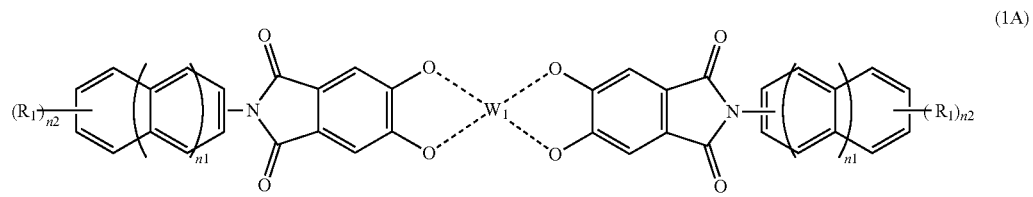
(1A)

wherein $W_1$ represents a tetravalent organic group, n1 represents an integer of 0 or 1, n2 represents an integer of 1 to 3, and $R_1$ represents any one or more of the following general formulae (1B)

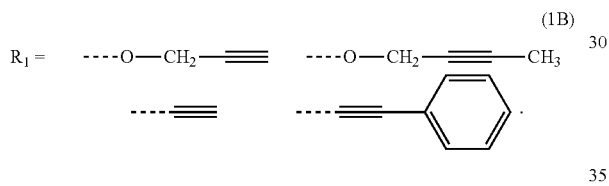
(1B)

22. The compound for forming an organic film according to claim 21, shown by the following general formula (1C) or (1D),

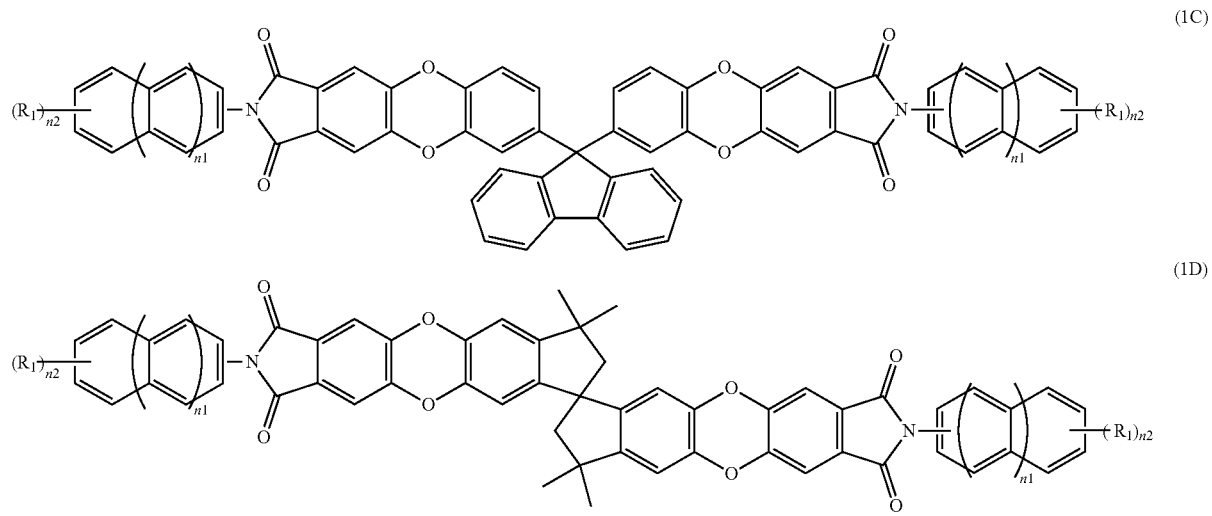
(1C)

(1D)

wherein n1, n2, and $R_1$ in the formulae have the same meanings as defined above.

23. The compound for forming an organic film according to claim 21, shown by the following general formula (1E) or (1F)

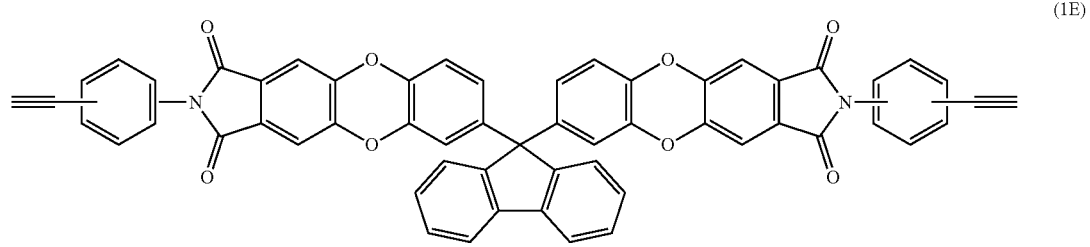
(1E)
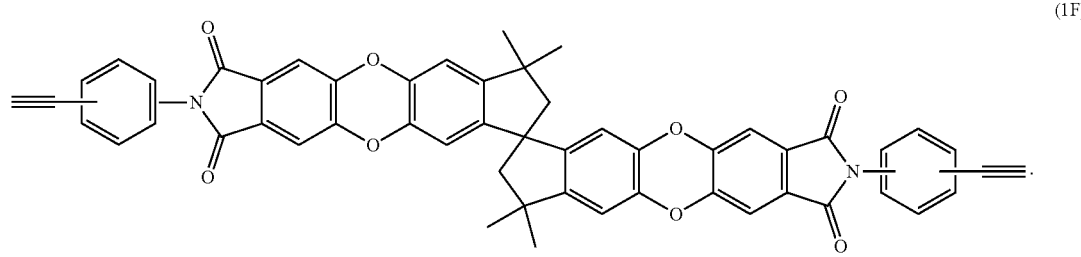
(1F)
\* \* \* \* \*